US005856112A

United States Patent [19]
Marley et al.

[11] Patent Number: 5,856,112
[45] Date of Patent: Jan. 5, 1999

[54] METHOD FOR SELECTIVELY INDUCING BIOMARKER EXPRESSION IN UROLOGIC TUMOR TISSUE FOR DIAGNOSIS AND TREATMENT THEREOF

[75] Inventors: Garry M. Marley; Robert W. Veltri, both of Oklahoma City, Okla.

[73] Assignee: UroCor, Inc., Oklahoma City, Okla.

[21] Appl. No.: 260,554

[22] Filed: Jun. 16, 1994

[51] Int. Cl.$^6$ .......................... G01N 33/574; C12N 5/02; C12N 5/06

[52] U.S. Cl. .................. 435/7.23; 435/7.24; 435/7.22; 435/375; 435/378; 435/383; 435/394; 436/543

[58] Field of Search .................................. 435/7.24, 7.23, 435/7.22, 240.1, 240.25, 240.21, 375, 378, 383, 394; 436/543

[56] References Cited

U.S. PATENT DOCUMENTS

| | | | |
|---|---|---|---|
| 4,495,288 | 1/1985 | Jarvis, Jr. et al. | 435/241 |
| 4,559,311 | 12/1985 | Stenman et al. | 436/542 |
| 4,582,799 | 4/1986 | Jarvis, Jr. | 435/68 |
| 4,839,046 | 6/1989 | Chandler | 210/355 |
| 4,988,623 | 1/1991 | Schwarz et al. | 435/286 |
| 4,994,374 | 2/1991 | Nishikawa et al. | 435/15 |
| 5,002,890 | 3/1991 | Morrison | 435/286 |
| 5,023,172 | 6/1991 | Djordjevic | 435/29 |
| 5,026,650 | 6/1991 | Schwarz et al. | 435/286 |
| 5,085,983 | 2/1992 | Scanlon | 435/6 |
| 5,104,802 | 4/1992 | Rhodes et al. | 435/286 |
| 5,153,118 | 10/1992 | Wright, Jr. et al. | 435/7.23 |
| 5,153,131 | 10/1992 | Wolf et al. | 435/240.24 |
| 5,153,132 | 10/1992 | Goodwin et al. | 435/240.24 |
| 5,153,133 | 10/1992 | Schwarz et al. | 435/240.24 |
| 5,155,034 | 10/1992 | Wolf et al. | 435/240.24 |
| 5,155,035 | 10/1992 | Schwarz et al. | 435/240.24 |
| 5,162,504 | 11/1992 | Horoszewicz | 530/388.2 |

FOREIGN PATENT DOCUMENTS

| | | |
|---|---|---|
| 0 529 659 | 3/1993 | European Pat. Off. . |
| 37 37 652 | 7/1989 | Germany . |
| 3 91491 | 4/1991 | Japan . |
| 3 160988 | 7/1991 | Japan . |

OTHER PUBLICATIONS

Donaldson, J. T., et al., *Int. J. Cancer*, 46, pp. 238–244, 1990.

Sacks, P. G., et al., *J. Cancer Res. Clin. Oncol.*, 118, pp. 490–496, 1992.

Bauer, et al., "Techniques for studies on growth characteristics of human prostate cancer cells," *Biotechnol Prog* 8:494–500 (1992).

Berkvig, R. "Tumor Spheroids from Biopsy Specimens," in *Spheroid culture in cancer research*, CRC Press, Boca Raton, 41–56, (1992).

Biran, et al., "Growth of human mammary carcinoma cells from biopsy specimens in serum–free medium on extracellular matrix," *Int J Cancer* 38:345–354 (1986).

Morimitsu, et al., "Morphologic characteristics, proliferation and tumor marker expression of two human ovarian carcinoma cell lines in three–dimensional culture," *Gynecol Oncol* 48:155–164 (1993).

Acker, Carlsson, and Stalnacke, "Electro–Physiological Measurements in Cultured Cellular Spheroids," *Acta. Path. Microbiol. Immunol. Scand.*, Sect. A, 91:151–160, 1983.

Carlsson and Brunk, "The Fine Structure of Three–Dimensional Colonies of Human Glioma Cells in Agarose Culture," *Acta. Path. Microbiol. Scand.*, Sect. A, 85:183–192, 1977.

Carlsson and Nederman, "Tumor Spheroids as a Model in Studies of Drug Effects," In Spheroid Culture in Cancer Research, CRC Press, Boca Raton, pp. 199–212, 1992.

Carlsson, "Tumor Spheroids in Studies of Immunotherapy," In Spheroid Culture in Cancer Research, CRC Press, Boca Raton, pp. 277–300, 1992.

Prewett, Goodwin and Spaulding, "Three–Dimensional Modeling of T-24 Human Bladder Carcinoma Cell Line: A New Simulated Microgravity Culture Vessel," *J. Tiss. Cult. Meth.*, 15:29–36, 1993.

Freyer, "Spheroids in Radiobiology Research," In Spheroid Culture in Cancer Research, CRC Press, Boca Raton, pp. 217–275, 1992.

Hoke, "Advanced Lab Bioreactors Extend Cell and Tissue Culture Capabilties," *The Scientist* pp. 17–18, Jul. 12, 1993.

Knüchel and Sutherland, "Cell Differentiation and Heterogeneity in Spheroid Culture," Spheroid Culture in Cancer Research, CRC Press, Boca Raton, pp. 159–170, 1992.

Marley et al., "Three–Dimensional In Vitro Culture of an Androgen–Refactory Prostate Cancer Cell Line Causes Alterations in Patterns of Biomarker Expressions," Proceedings of the American Association for Cancer Research, 38:544, Mar. 1997.

Marley et al., "DNA Content and F–Actin Expression Within Human Glioma Spheroids Cultured In Vitro," *J. Cell Biol.*, 115:227a, 1991, Abstract No. 1320.

Meikle and Smith, "Epidermiology of Prostate Cancer," *Urologic Clinics of North America*, 17(4):709–718, Nov. 1990.

Nederman et al., "Demonstration of an Extracellular Matrix in Multicellular Tumor," *Cancer Research*, 44:3090–3097, Jul. 1984.

Nederman and Twentyman, "Spheroids for Studies of Drug Effects, " *Recent Results in Cancer Research*, 95:84–102, 1984.

Parent–Vaugeois et al., "Variavle Modulation of Expression of Two Superficial Human Bladder Tumor Associated Antigens by Spatial Configuration of Cell Populations" Proceedings of the American Association for Cancer Research, 30:355, Mar. 1989 Abtract No. 1410.

(List continued on next page.)

*Primary Examiner*—Toni R. Scheiner
*Attorney, Agent, or Firm*—Arnold White & Durkee

[57] ABSTRACT

A method for selectively inducing expression of biomarkers for urologic cancers, including prostate and bladder cancer, is disclosed. Tumor cells are cultured using a low shear rotational three-dimensional technique under conditions effective to induce said selective expression. The method is useful for diagnostic and therapeutic applications.

27 Claims, 9 Drawing Sheets

OTHER PUBLICATIONS deVere et al., "Prognosis in Disseminated Prostate Cancer as Related to Tumor Ploidy and Differentiation," World J. Urol., 8:47–50, 1990.

Sutherland, "Cell and Environment Interactions in Tumor Microregions: The Multicell Spheroid Model," Science, 240:177–184, Apr. 1988.

Sutherland and Durand, "Growth and Cellular Characteristics of Multicell Spheroids," Recent Results in Cancer Research, 95:24–49, 1984.

Van Moorselaar et al., "Combined Effects of Tumor Necrosis Factor Alpha and Radiation in the Treatment of Renal Carcinoma Grown as Radia Spheroids," Anticancer Research, 10:1769–1774, 1990.

Veltri et al., "DNA/F–Actin Analysis of a Potential In Vitro Glioma Model," Proceedings of the American Association for Cancer Research, May 21, 1992, Abstract No. 251.

Olive and Banath, "Growth Fraction Measured in WiDr Human Colon Carcinoma Speroids and Xenografts Using Comet Assay," Proceedings of the American Association for Cancer Research, May 21, 1992, Abstract No. 252.

Veltri et al., "DNA Content and Tumor Biomarker Expression from a Novel Spheroidal In Vitro Prostatic Human Tumor Model," Proceedings of the American Association of Cancer Research Annual Meeting May 20, 1993 Orlando, Florida.

Marley, Gonda and Ingram, Human Glioma Spheroid Formation in the NASA–JSC Bioreactor, J. Cel Biol., 3:481a, 1990. Abstract No. 2697.

Sutherland and Carlsson, "Spheroids in Cancer Research," Cancer Research, 41:2980–2994, 1981.

Beckett, et al., "Monoclonal antibody PD–41 recognizes an antigen restricted to prostate adenocarcinomas," Cancer Res 51:1326–1333 (1991).

Cordon–Cardo, et al., "Immunopathologic analysis of human bladder cancer: characterization of two new antigens associated with low–grade superficial bladder tumors," Am J Pathol 140:375–385 (1992).

Diamond, et al., "Computerized image analysis of nuclear shape as a prognostic factor for prostatic cancer," The Prostate 3:321–332 (1982).

Fradet, et al., "Polymorphic expression of a human superficial bladder tumor antigen defined by mouse monoclonal antibodies," Proc Natl Acad Sci USA 84:7227–7231 (1987).

Fradet, Yves, "Markers of prognosis in superficial bladder cancer," Seminars in Urology X:28–38 (1992).

Gleason, D.F., "Prediction of prognosis for prostatic adenocarcinoma by combined histological grading and clinical staging," J Urology 111:58–64 (1974).

Gleason, D.F., "Histological grading of prostate carcinoma," In: Contemporary Issues in Surgical Pathology of the Prostate. D.G. Bostick (ed.), Churchill Livingstone, Edinburgh, pp. 83–93 (1990).

Kuhn, et al., "Expression of the c–erbB2 (HER–2/neu) oncoprotein in human prostatic carcinoma," J Urology 150:1427–1433 (1993).

Lineham, et al., "Metastatic models and molecular genetics of prostate cancer," J Natl Cancer Inst 84:914–915 (1992).

Lipford, et al., "Comparative study of monoclonal antibodies TURP–27 and HNK–1: their relationship to neural cell adhesion molecules and prostate tumor–associated antigens," Cancer Res 51:2296–2301 (1991).

Mueller–Klieser, W. "Multicellular spheroids: a review on cellular aggregates in cancer research," J Cancer Res Clin Oncol 113:101–122 (1987).

Partin, et al., "A comparison of nuclear morphometry and Gleason grade as a predictor of prognosis in stage A2 prostate cancer a critical analysis," J Urology 142:1254–1258 (1989).

Partin, et al., "Use of nuclear morphometry, Gleason histologic scoring, clinical stage, and age to predict disease–free survival among patients with prostate cancer," Cancer 70:161–168 (1992).

Peters, et al., "Prognostic significance of the nuclear DNA content in localized prostate adenocarcinoma," Anal Quant Cytol Histol 12:359–365 (1990).

Pressman, N.J., "Markovian an analysis of cervical cell images," J Histochem Cytochem 24:138–144 (1976).

Starling, et al., "Human prostate tissue antigens defined by murine monoclonal antibodies," Cancer Res. 46:367–374 (1986).

Stevenson, et al., "Flow Cytometry of Prostate Cancer: Relationship of DNA Content to Survival," Cancer Res 47:2504–2509 (1987).

Thompson et al., "Multistage carcinogenesis induced by ras and myc oncogenes in a reconstituted organ," Cell 56:917–930 (1989).

Thompson, T.C., "Growth factors and oncogenes in prostate cancer," Cancer Cells 2:345–354 (1990).

Tjota, et al., "Murine monoclonal antibodies reactive with a variety of androgen independent Dunning rat prostate adenocarcinoma sublines are also reactive with human prostate adenocarcinoma," J Urol 146:205–212 (1991).

Ware et al., "Immunohistochemical detection of c–erbB2 protein in human benign and neoplastic prostate," Human Pathology 22:254–258 (1991).

Wright, et al., "Generation and characterization of monoclonal antibodies to prostate secretory protein (PSP)," Int J Cancer 46:39–49 (1990).

Wright, et al., "Immunohistochemical evaluation of the expression of prostate tumor–associated markers in the nude mouse human prostate carcinoma heterotransplant line PC–82, PC–EW, and PC–EG," The Prostate 17:301–316 (1990).

Wright, et al., "A novel prostate carcinoma–associated glycoprotein complex recognized by monoclonal antibody TURP–27," Int J Cancer 47:717–725 (1991).

Yuhas, et al., "A simplified method for production and growth of multicellular tumor spheroids," Cancer Res 37:3639–3643 (1977).

METHOD FOR SELECTIVELY INDUCING BIOMARKER EXPRESSION IN UROLOGIC TUMOR TISSUE FOR DIAGNOSIS AND TREATMENT THEREOF

TECHNICAL FIELD

This invention relates to the field of tissue-culturing of mammalian cells for purposes of diagnosing and treating neoplastic disease.

BACKGROUND OF THE INVENTION

Tissue culturing of mammalian cells has become a preferred technique for scientists to study various aspects of cancer, including its etiology and its treatment. A convenient form of tissue culturing is known as two-dimensional monolayer cell culturing. In this technique, cells admixed with appropriate life-sustaining media are placed in a specially-treated plastic petri dish or flask. The cells adhere to the bottom surface of the container, assuming a characteristic flattened pattern during spreading, and replicate on that surface as a single layer, called a monolayer. The media remains on top of the flat layer of cells and is changed periodically to provide the growing cells with essential nutrients. The container wall surface area determines the number of cells that can be effectively cultured. When it is desired to split the cultures, an enzyme such as trypsin is utilized to destroy the anchorage of the cells to the dish so that subcultures can be made. While the cells are in culture, various agents can be applied to the media in the plates and the effect on the cells observed. For example, suspected carcinogens can be added to individual cultures of non-cancerous cells to ascertain if the carcinogen causes the cells to exhibit the growth pattern characteristic of cancerous cells. Tissue culture offers an effective screening tool that increases the number of agents that can be rapidly screened as compared to using animals for the same purpose. With regard to potential treatment of cancerous disease, tissue culture may be used to determine if experimental drugs or antibodies would be effective in destroying cancerous cells. Tissue culture can also be used to attempt to determine whether particular antibodies might bind to cancer cells in order to provide for targeting of particular cells with drugs conjugated to such antibodies.

Even though two-dimensional monolayer tissue culture has provided great benefits to scientists and clinicians, it suffers from a lingering disadvantage as well. Tumors do not grow two-dimensionally in the body, and therefore, monolayer cultures of tumor cells cannot reflect their true in vivo three-dimensional growth architecture. In addition, monolayer cultures reflect a homogeneous cell population in which every cell is exactly like every other cell in culture. This is not the case for solid tumors, which are vascularized within the host and most often exhibit a heterogenous cell population believed to result from cell differentiation induced by differences in biochemical environment such as hormones, growth factors, oxygen tension, and catabolic waste products between blood vessels and the tumor core. The solid tumor has a population of dynamic cells, meaning that they may be constantly changing in response to their environment. Cells may exhibit different morphological, biochemical and histological properties.

In an attempt to more closely model the in vivo tumor, three-dimensional tissue culture has been developed. One technique of three-dimensional tissue culturing is the spinner flask technique. W. Mueller-Klieser, "Multicellular Spheroids," *J Cancer Res Clin Oncol* 13:101–122 (1986).

Another technique is the liquid-overlay technique. J. M. Yuhas, et al., "A simplified method for production and growth of multicellular tumor spheroids," *Cancer Res* 37:3639–3643 (1977). While three-dimensional growth can be achieved by these techniques, it may be limited as to size and development. Another three-dimensional technique is that developed by the National Aeronautic And Space Agency ("NASA") which is a rotating culture vessel specifically engineered to randomize the gravity vector by rotating a fluid-filled culture vessel about a horizontal axis while suspending cells and cell aggregates with minimum fluid shear. These devices have been described in U.S. Pat. Nos. 5,153,131; 5,153,132; 5,153,133; 5,155,034; and 5,155,035. A commercial device for three-dimensional cell culturing is known as the High Aspect Rotating Vessel (HARV) and is manufactured by Synthecon, Inc. (Friendswood, Tex.). The HARV vessel, or bioreactor, rotates cells and medium in a disk-shaped 50 ml growth chamber about a horizontal axis with zero head space, resulting in low fluid shear conditions. Adequate gas exchange is maintained across a siliconized rubber membrane which lines one face of the chamber.

Despite the advent of three-dimensional cell culturing techniques, many obstacles remain in the diagnosis and treatment of cancer. The techniques are available as tools, but these tools have not been implemented in the prior art to provide a diagnostic tool for urological cancers, such as prostate and bladder cancer.

Prostate cancer is the most common non-cutaneous malignant disease among American males, and presumably is also a world-wide health problem. The incidence of prostate cancer increases more rapidly with age than any other type of cancer. Prostate cancer often causes death while remaining undiagnosed. A. W. Meikle, et al., "Epidemiology of prostate cancer," in *Early Detection and Treatment of Localized Carcinoma of the Prostate.* J. A. Smith (ed.) Saunders, Phila., pp. 709–718 (1990).

At present, prostate cancer, or adenocarcinoma (defined as a malignant neoplasm of epithelial cells in glandular or gland-like pattern), has been diagnosed or predicted from histologic grading, staging, tumor volume and a multiparameter predictive factor score (PFS). D. F. Gleason, "Prediction of Prognosis for Prostatic Adenocarcinoma by Combined Histological Grading and Clinical Staging," *J Urol* 111:58–64 (1974); D. F. Gleason, "Histological Grading of Prostate Carcinoma," in *Contemporary Issues in Surgical Pathology of the Prostate.* D. G. Bostwick (ed.), Churchill Livingstone, Edinburgh, pp. 83–93 (1990); Partin et al., "Use of nuclear morphometry, Gleason histologic scoring, clinical stage, and age to predict disease-free survival among patients with prostate cancer," *Cancer* 70:161–168 (1992); Partin, et al., "A comparison of nuclear morphometry and Gleason grade as a predictor of prognosis in stage A2 prostate cancer: a critical analysis," *J Urol* 142:1254–1258 (1989). The success of these predictive methods depends heavily on the subjective and selective objective interpretative skills of a clinician.

To eliminate the subjective nature of histologic analysis described above, the art has suggested that biomarkers be observed. The term "biomarker" can be generally defined as a genetically determined product expressed as antigenic proteins, glycoproteins or other biomolecules detectable by antibody probes. These include growth factors, hormones, receptors, oncogenes, cytoskeletal and nucleoskeletal proteins, tumor suppressor gene products, differentiation molecules or organ-restricted neoantigens.

Nuclear morphometric measurements, or "shape descriptors" have prognostic value in determining the clinical outcome of prostatic malignancies. Pressman, N.J., "Markovian analysis of cervical cell images," *J Histochem Cytochem* 24:138–144 (1976). Nuclear shape is a function of the interaction of nuclear proteins and cytoplasmic structural determinants. Diamond et al demonstrated that nuclear roundness could distinguish prostatic tumors with high metastatic potential from those that would eventuate as more indolent tumors. Diamond et al., "Computerized image analysis of nuclear shape as a prognostic factor for prostatic cancer," *The Prostate* 3:321–332 (1982). Partin et al utilized variance of nuclear roundness incorporating it into the multi-parameter predictive factor score (PFS) mentioned above. Partin et al., *Cancer* 70:161–168 (1992). Three-dimensionality provides a micro-milieu in which these determinants can more realistically recreate an in vivo-like interdependence.

One biomarker that has been followed in the art to determine the progression of disease is DNA ploidy analysis. The term "ploidy" refers to the state of the cell nucleus with respect to the number of genomes it contains. A genome is the complete set of chromosomes derived from one parent, or haploid number, so in a normal non-gametic cell, the ploidy is diploid. Cancer cells may be diploid, tetraploid, or aneuploid (having an abnormal number of chromosomes, not an exact multiple of the haploid number). DNA ploidy analysis has been found to be of prognostic significance in selected prostate cancers. J. M. Peters, et al., "Prognostic significance of the Nuclear DNA Content in Localized Prostatic Adenocarcinoma," *Anal Quant Cytol Histol* 12:359–365 (1990); R. W deVere White, et al., "Prognosis in Disseminated Prostate Cancer As Related to Tumor Ploidy and Differentiation," *World J Urol* 8:47–50 (1990); R. A. Stevenson, et al., "Flow Cytometry of Prostate Cancer: Relationship of DNA Content to Survival," *Cancer Res* 47:2504–2509 (1987).

While a correlation between DNA ploidy patterns and prognostics has been established, data have also suggested that the ploidy patterns may vary between the peripheral zone and the central zone of tumor specimens. However, three-dimensionally cultured cells and tissue-like aggregates have not been used for the purpose of patient-specific diagnosis, monitoring, and therapeutics, i.e., identification of patterns of biomarker panel expressions and the identification of new biomarkers as neoantigens within individual clinical patients.

Another positive marker of cellular differentiation in the malignant or premalignant state has been reported to be the increased level of f-actin, a polymerized form of actin, a ubiquitous cytoskeletal protein in eukaryotic cells associated with cellular motility and morphology, intracellular transport, secretion and cell division.

Cancer of the prostate may also be regulated by cellular oncogenes or tumor suppressor genes. In an isogenic male murine host, retrovirally introduced myc and ras oncogenes induced hyperplastic and dysplastic pathologies, respectively, in the reconstituted fetal urogenital sinus model. Myc+ras in combination induced carcinomas. Thompson et al., "Multistage carcinogenesis induced by ras and myc oncogenes in a reconstituted organ," *Cell* 56:917–930 (1989). The same mouse model noted a strong association of Transforming Growth Factors (TGF), i.e., TGF-β1 and TGF-β3 in prostatic tumor progression. Thompson, T. C., "Growth factors and oncogenes in prostate cancer," *Cancer Cells* 2:345–354 (1990). The c-erbB2 (HER-2/neu) oncogene product has been detected immunohistochemically at significant levels in human prostatic carcinomas. Kuhn et al., "Expression of the c-erbB2 (HER-2/neu) oncoprotein in human prostatic carcinoma," *J Urol* 150:1427–1433 (1993); Ware et al., "Immunohistochemical detection of c-erbB2 protein in human benign and neoplastic prostate," *Human Pathology* 22:254–258 (1991).

High levels of the ras oncogene have been detected in malignant prostate and benign prostatic hypertrophy (BPH) specimens. Higher levels of c-myc messenger RNAs have been reported in human adenocarcinoma than in BPH. Abnormal expression of p53 tumor suppressor gene has been demonstrated in at least two prostate carcinoma cell lines. The Rb, or retinoblastoma gene product, expression may be impaired or defective in human prostate carcinomas as are other markers of metastatic disease.

Another biomarker of metastatic prostatic disease is Prostatic Specific Antigen (PSA). This is a serum-based biomarker and is generally recognized as a good indicator of prognosis, but a significant number of false positive radio-immunoassays will occur in cases of BPH. W. M. Lineham, et al., "Metastatic models and molecular genetics of prostate cancer," *J Natl Cancer Inst* 84:914–915 (1992).

Other biomarkers that have been elucidated are TURP-27 (G. L. Wright, et al., "A novel prostate carcinoma-associated glycoprotein complex recognized by monoclonal antibody TURP-27," *Int J Cancer* 47:717–725 (1991); G. L. Wright, et al., "Immunohistochemical evaluation of the expression of prostate tumor-associated markers in the nude mouse human prostate carcinoma heterotransplant line PC-82, PC-EW, and PC-EG," *The Prostate* 17:301–316 (1990)), PSP-19 (G. L. Wright, et al., "Generation and characterization of monoclonal antibodies to prostate secretory protein (PSP)," *Int J Cancer* 46:39–49 (1990); G. L. Wright, et al., *The Prostate* 17:301–316 (1990)) and PD-41 (M. L. Beckett, et al., "Monoclonal antibody PD-41 recognizes an antigen restricted to prostate adenocarcinomas," *Cancer Res* 51:1326–1333 (1991); G. L. Wright, et al., *The Prostate* 17:301–316 (1990)). Another marker binds to monoclonal antibody MCA-R1 but does not bind to BPH-associated tissue. A. Tjota, et al., "Murine monoclonal antibodies reactive with a variety of androgen independent Dunning rat prostate adenocarcinoma sublines are also reactive with human prostate adenocarcinoma," *J Urol* 146:205–212 (1991).

Superficial transitional cell bladder cancer is another form of urological carcinoma which is commonly diagnosed and treated in the early stages of tumor development and is potentially curable. However, recurrence of the bladder cancer occurs in over 50% of patients after successful initial treatment, and in about 30% of the patients, recurrence progresses to infiltrating cancer. Because of the variability in clinical behavior in individuals, patient management requires a constant monitoring of the bladder. Clinical methods of predicting recurrence and disease progression include tumor staging, tumor size and patient's previous recurrence rate. Biological predictors have been described for testing both tumor specimens and exfoliated cells which include DNA ploidy, oncogene or tumor suppressor gene activation or inactivation (e.g., H-ras, c-erbB2, Rb, p53), rate of epidermal growth factor expression (e.g., AMFr, autocrine motility factor), and the reaction of specific monoclonal antibodies to antigens selectively expressed on bladder tumors. For example, monoclonal antibodies to the highly restricted tumor-associated M-344 and 19a211 antigens having been characterized as biomarkers of high specificity for papillary superficial bladder tumors and carcinoma in situ, whereas T43 and T138 antigen expression is associated with progression to invasive cancer. Cordon-Cardo, et al., "Immunopathologic analysis of human urinary bladder cancer. Characterization of two new antigens associated with low-grade superficial bladder tumors," *Am J of Pathology* 140:375–385 (1992); Fradet, Yves, "Markers of prognosis in superficial bladder cancer," *Seminars in Urology* X:28–38 (1992)

It has now been found that three-dimensional culturing techniques can be employed to induce selective differentiation of phenotypic, nuclear morphometric parameters, motility and genotypic markers on tumor cells associated with urological cancers, specifically prostate and bladder adenocarcinoma. The use of three-dimensional culturing techniques is superior to both the use of two-dimensional techniques and the study of biopsied tissue specimens because the three-dimensional culture is believed to more closely resemble the in vivo dynamic tumor tissue. The method of this invention is useful for diagnostic and therapeutic applications.

SUMMARY OF THE INVENTION

Figure 1:
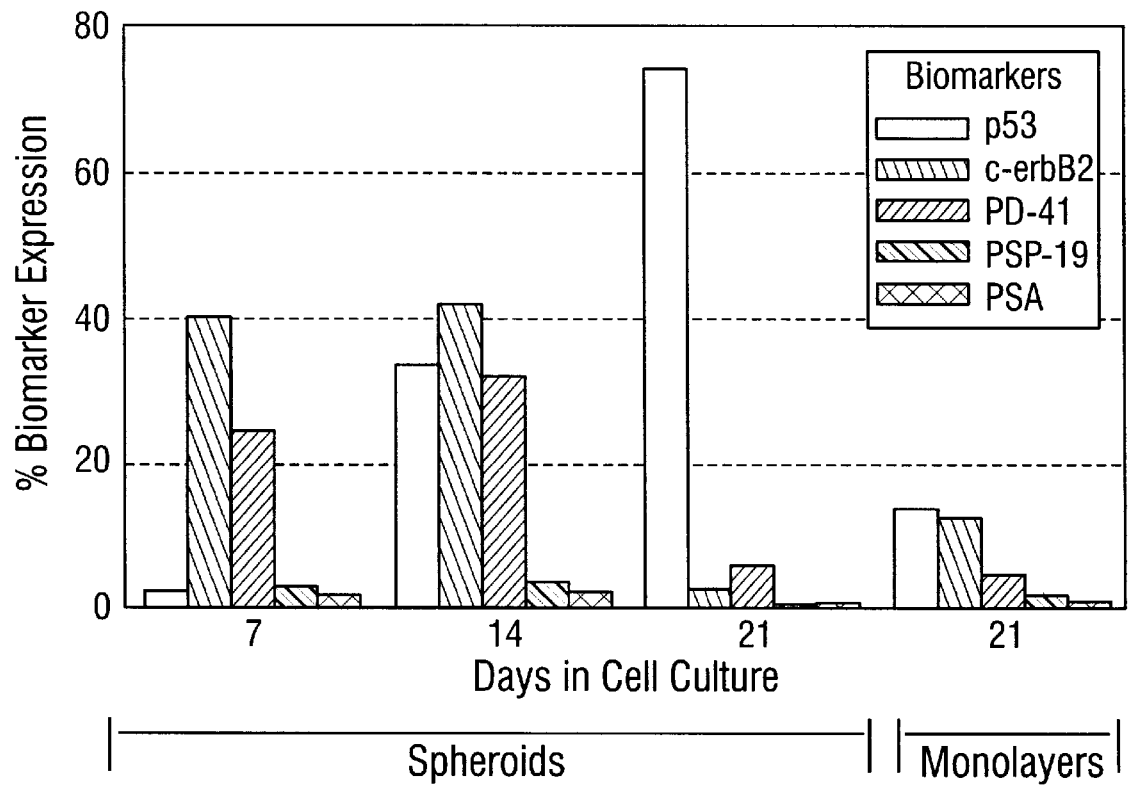
FIG. 1 is a graphical depiction of biomarker expression rates in PC3-MF prostate adenocarcinoma cell line grown in the High Aspect Ratio Vessel (HARV) bioreactor.

In one aspect of the invention, tumor cells are cultured in a three-dimensional environment under conditions which will effectively induce biomarker or neoantigen expression. Once biomarkers are associated with particular types of cancer, patient samples can be cultured in three-dimensions and assayed for biomarkers to determine the presence, absence or extent of disease. In another aspect of the invention, the patient culture can be used to screen potential therapies by monitoring quantitative changes in biomarker expression after treatment with antineoplastic agents. In another aspect of the invention, a three-dimensional culture of tumor cells may be used to test for the presence of tumor-specific cytotoxic lymphocytes or antibodies in a patient sample and to isolate the same by binding the same to antigens expressed on the three-dimensional tumor cell cultures. In another embodiment, antigens expressed by three dimensional tumor cell cultures can be used to develop vaccines by isolating the antigen and using it to raise an immunogenic response in an animal.

In a preferred embodiment, three-dimensional tissue culture techniques are used to identify markers for urological cancers such as prostate and bladder, and as diagnostic tools for identifying and treating the same.

DETAILED DESCRIPTION OF THE INVENTION

Three-dimensional tissue culturing of tumor cells, preferably urological cancer cells such as prostate and bladder cancer cells, are cultured under conditions effective to induce the selective expression of tumor biomarkers. This selective expression is useful because assays for diagnostic purposes can now employ the differential expression of these markers to assess prognostics of the tumor. Further, identification of markers more prevalent in three-dimensional culture allows such cultures to be used as a model of in vivo tumors, and such three-dimensional cultures can be used by physicians and scientists to determine the best course of treatment and/or prevention for patients at high risk or afflicted with tumors. This can be done by testing the response of the three-dimensional tumors and the identified biomarkers to chemopreventive and therapeutic agents. The three-dimensional cultures can also be used to find new antigens, or neoantigens, expressed on the surface and exterior of tumor cells. Because the three-dimensional culture correlates better to in vivo tumors vis-a-vis two-dimensional (monolayer) cultures, such neoantigens are expected to be highly efficacious for selection of antigen-specific T-cell clones for tumor-specific immunotargeting such as in the preparation of tumor-specific vaccines.

The cells that are to be grown in three-dimensional culture are selected from established tumor cell lines, cell lines developed from patient tumors, and biopsies of patient tumors. The criteria for cell selection are morphological, biochemical, and/or genetic. Characteristics optimal for good three-dimensional culture include synthesis of extracellular matrix (ECM) molecules, in particular, cellular adhesion molecules (CAMs) and the ability to survive in heterogeneous environments of nutrients and oxygen as found within the in vivo milieu. Even if significant quantities of ECM are not synthesized by the cell type, biocompatibility in an artificial matrix such as MATRIGEL™ (Collaborative Biomedical Products, Becton Dickinson Labware, Two Oak Park, Bedford, Mass. 01730), or its tissue culture flask form MATRIGEL™ BIOCOAT, can be used to determine candidacy for three-dimensional culture.

Anchorage-dependent cell lines studied can be enriched for those forming macroscopic aggregates by utilizing the following techniques: modified liquid-overlay agarose colonies (Yuhas, et al., "A simplified method for the production and growth of multicellular spheroids," *Cancer Res* 37:3639 (1977)), followed by either low speed centrifugation (100× g; 5 minutes) or Percoll gradient preparation to separate out larger aggregates for reinoculation.

Any three-dimensional tissue culturing technique may be used. It is preferred that liquid spinner cultures, liquid-overlay agarose cultures, or culturing in a bioreactor such as the High Aspect Ratio Vessel (HARV) or similar apparatus be employed. Most preferred is use of the HARV bioreactor, since the cells are not subject to shear forces using this technique.

The conditions selected for the three-dimensional tissue culture technique are important for the successful selective induction of biomarkers. Selection of optimal culture milieu for three-dimensional culture should be based upon conditions which promote optimal cell viability, nutrient turnover (as evidenced by positive rates for glucose uptake, oxygen consumption, carbon dioxide production and acid pH production), cell-to-cell adhesion, cell growth and reproduction, optimal and stable three-dimensional volumes (with viability at equilibrium) which reflect the heterogeneity of the micro environment of the in vivo tumor.

Once the three-dimensional culture is established, it can be manipulated in various ways. The culture can be used to test chemoprevention protocols for efficacy, so that similar tumors afflicting patients can be treated in vivo with protocols found to be effective on the culture tumor. Three-dimensional cultures grown from cells from biopsied tissue can be tested for markers known to be associated with cancer cells for diagnostic purposes. Antibodies can be applied to the culture in order to assess binding capabilities to antigens expected to be expressed in both three-dimensional cultures and in vivo. Antibodies capable of binding to the three-dimensional cultures may then be identified as likely candidates for therapy either alone or conjugated to a tumor-destroying drug. Neoantigens may be isolated and used to raise antibodies which will bind to tumors. For example, PD-41 is a prostate tumor-associated neoantigen which is not produced by normal tissue. During prostate carcinogenesis, PD-41 would be recognized as a foreign protein, inducing both humoral and cell-mediated immune response in a patient. Using three-dimensional aggregates expressing PD-41 in a binding assay, the patient's tumor-specific cytotoxic lymphocytes or antibodies can then be isolated and vaccines to immunize against the cancer or its invasive properties can also be produced. Neoantigens have been identified with bladder cancer (e.g., M-344, ras p-21 and p53) and other forms of cancer such as pancreatic, colon, and breast cancer (e.g., MUC-1 gene products, ras p-21, and p53) which can be similarly exploited in three-dimensional culturing. Surrogate three-dimensional biomarker profiles may be used to develop new treatments, preventive therapy protocols, and monitoring protocols. The efficacy of therapeutics may be monitored on an individual basis by monitoring modulation of patient-specific panels of biomarker expressions. Three-dimensional cultures may also be used to replace in vivo animal models based on morphologic, biochemical, antigenic, and genetic fidelity.

Differential expression of biomarkers between two-dimensional culture and three-dimensional culture is important for utilitarian use of this invention. Three-dimensional culture may be used for immunoselection of cytotoxic killer T-cells and isolation of T-cell clones for expansion and use in adoptive immunotherapy; an immunogen to identify unknown neoantigens; a target for cytotoxic T-cell assays in patients undergoing immunotherapy by active or passive modalities; generation of in vivo-like biomarker controls for diagnostic assays (service or kits); and source of cells for motility/invasiveness testing.

EXAMPLE 1

Determination of Immunohistochemistry of Prostate Cell Cultures

Differential expression of biomarkers was evaluated as a method of characterizing prostate cell cultures. Prostatic three-dimensional spheroidal aggregates (from culturing methodology given in A–C below) and two-dimensional monolayers (from culturing methodology given in D below) were harvested and processed simultaneously. Following post-fixation (described in A–C below), spheroidal aggregates were minced into fine pieces with a #3 scalpel prior to further processing. Cells were washed in phosphate-buffered saline (PBS) (pH 7.2) at room temperature, pelleted at 500×g, resuspended and washed a second time. Cells were incubated with 10% rabbit serum. for 30 minutes at 37° C. Cells were pelleted (500×g) for 5 minutes. Supernatant was aspirated and cells incubated with appropriate dilution of a mouse monoclonal antibody, i.e., a 1:10 dilution of a 50 $\mu$g/ml stock solution for $\alpha$-PD-41 (described in M. L. Beckett et al., "Monoclonal antibody PD-41 recognizes an antigen restricted to prostate adenocarcinomas," *Cancer Res* 51:1326–1333 (1991); or a 1:20 dilution of a 0.1 mg/ml stock solution of $\alpha$-p53 (Ab-2; clone 1801) (Oncogene Science; Cambridge, Mass.). Prior to addition of the p-53 antibody, cells were permeabilized with 0.1% Triton X-100 (Sigma Chemical Co.; St. Louis, Mo.), for 5 minutes, pelleted as described above and washed with PBS. Supernatants were aspirated, and 100 $\mu$l of working monoclonal antiserum was added to each cell pellet in a disposable plastic tube. The tubes were capped, gently mixed and incubated overnight (16 hours) at 4° C. Samples were subsequently washed twice in PBS (pH 7.2), pelleted, and incubated for 30 minutes (4° C.) with a fluoresceinconjugated goat anti-mouse antibody (8.5 μg/ml) (Coulter Immunology, Hialeah, Fla.). Secondary antiserum was washed twice with cold PBS, resuspended in PBS and assayed for fluorescence intensity. Mouse isotypic controls antisera (5 μg/ml) were incubated under identical conditions.

Figure 7:
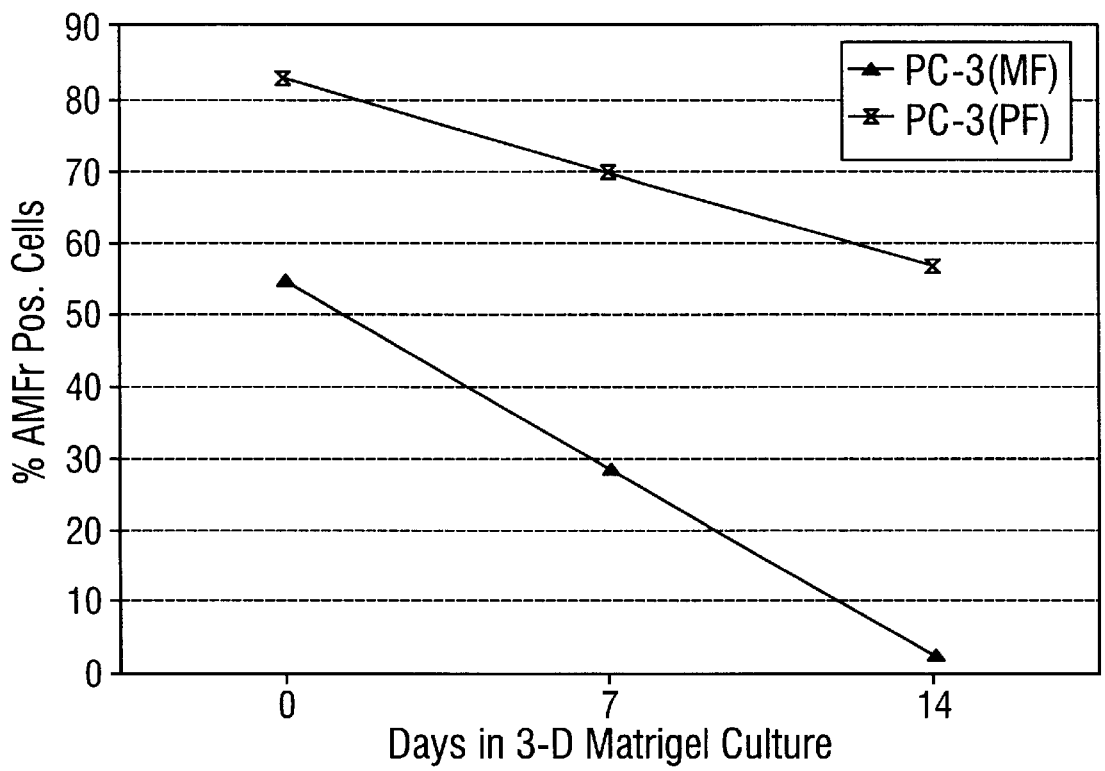
FIG. 7 is a graph depicting the percentage of cells positive for AMFr (automotility factor receptor) antigen expression in three-dimensional cultures of prostate carcinoma cell lines PC3-MF and PC3-PF embedded in MATRIGEL™ matrix on agarose-coated plates measured over two weeks by flow cytometry.
Figure 8:
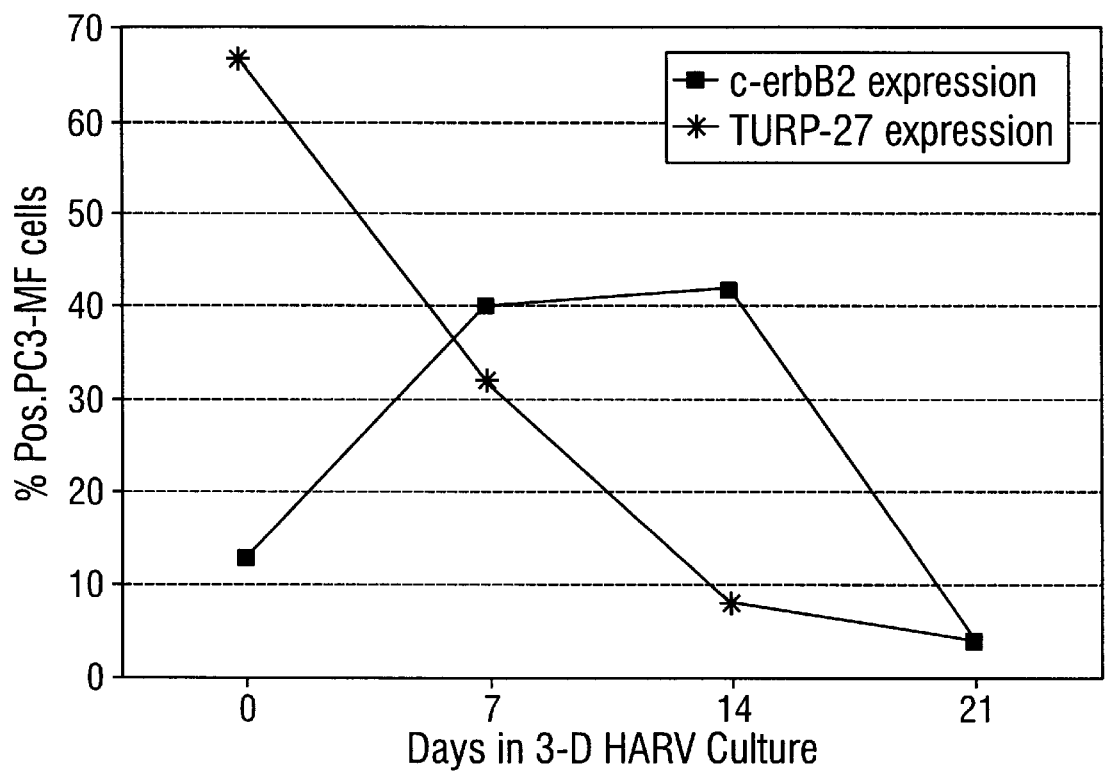
FIG. 8 is a graph depicting the percentage of cells positive for c-erbB2 and TURP-27 antigen expression in three-dimensional cultures of prostate carcinoma cell line PC3-MF in the HARV bioreactor measured over three weeks by flow cytometry.
Figure 9:
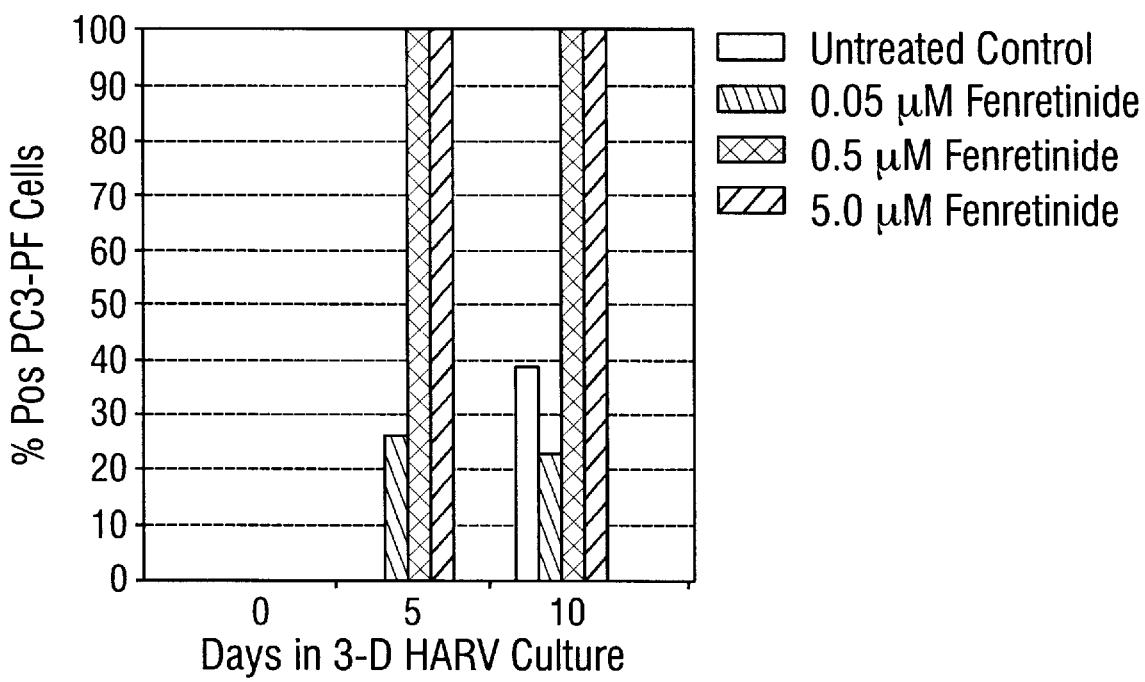
FIG. 9 is a graph depicting the induction of TURP-27 antigen expression by fenretinide (4HPR) in three-dimensional cultures of prostate carcinoma cell line PC3-PF in the HARV bioreactor measured over ten days by flow cytometry.

Fluorescence intensity was quantitated on the EPICS Elite Flow Cytometer (Coulter, Hialeah, Fla.) utilizing the example parameters: 25 mW argon laser; filters: 488 nm dichroic, 457 nm 502/long pass blocking, 550 nm long pass dichroic, 525 nm band pass; excitation wavelength: 488 nm; sample flow rate: 17 μl/ml; sheath pressure: 7.5 psi; sample vol: 150 μl. To determine the absolute percentage of positively reactive cells, REPROMAN (True Facts Software, Seattle, Wash.) software package was used for listmode or histogram data files. Statistical analysis for multiple integration regions and normalization of histogram counts was performed on each data set. Biomarkers analyzed included the following: PD-41, pan-ras, E-cadherin, TCSF (tumor collagenase stimulating factor), p53, and AMFr (automotility factor receptor). FIG. 4–FIG. 8 illustrate the up-regulation of PD-41, pan-ras, E-cadherin, TCSF, and p53, and FIG. 9 presents the down-regulation of AMFr.

A. Culturing of Prostate Cells Using The High Aspect Ratio Vessel (HARV) Bioreactor Monolayers of prostate carcinoma cells (malignant prostate carcinoma cell line PC3-MF (passage 27), originally established from a resected prostate tumor bone. metastasis, was obtained from Dr. George Wright, Jr. (Eastern Virginia Medical School). M. E. Kaighn, et al., "Establishment and characterization of a human prostatic carcinoma cell line (PC-3)," *Invest Urol* 17:16 (1979) These cells were cultured in large flat tissue culture flasks (Corning; Corning, N.Y.), were trypsinized (0.25% trypsin-EDTA; 37° C.; 10 minutes), and centrifuged at 1000 rpm in medium consisting of RPMI 1640 (Gibco-BRL; Grand Island, N.Y.) and supplemented with 25 mM HEPES, 10% defined fetal bovine serum (Hyclone; Logan, Utah), plus 100 units/ml of penicillin and 100 μg/ml of streptomycin. The High Aspect Rotating Vessel (HARV) bioreactor was inoculated with 50 ml of the medium described above, pre-warmed to 37° C., into which had been resuspended $4.0 \times 10^5$ cells/ml. The vessel was rotated in a humidified 5% $CO_2$ incubator (37° C.) at a rate to maintain cellular aggregates in constant suspension. A pH of 7.2–7.3 was rigorously maintained during the three week culture period by daily replacement of 20 ml of conditioned culture medium with fresh medium. Vessel rotation rates were initially set at 40 rpm and adjusted to 22 rpm during the first 48 hours of the experiment in order to maintain suspension of growing spheroids and to minimize collisions with the vessel wall.

During each time point for collection, the HARV bioreactor was removed from its base, placed in a sterile tissue culture hood and positioned for 10 minutes along its width. In this manner, larger spheroidal aggregates could preferentially settle closer to the syringe port. Viable cells or aggregates not harvested were immediately re-inoculated into the vessel.

In the fixation procedure for antigens, prostate cell aggregates were harvested by a 10 ml syringe from the HARV bioreactor. For surface antigens, the cell aggregates were washed twice with cold RPMI 1640 (without supplements), resuspended in cold RPMI 1640 16 h medium in the presence of 1% methanol-free formaldehyde (Polysciences, Malvern, Pa.) (4° C.; 30 minutes). In the fixation of nuclear antigens for nuclear matrix protein (NMP-100) fluorescent immunocytochemistry, cells were fixed in 50% ethanol (instead of 0.5% formaldehyde) in RPMI 1640 culture medium without supplements and maintained for 16 hours at 4° C.

B. Culturing of Prostate Cells Using Spinner Flask Cultures

Spinner flask cultures were initiated by utilizing a variation of the method first applied by A. Moscona, "Cell suspensions from organ rudiments of chick embryos," *Exp Cell Res* 3:535 (1952). Spinner flasks (Bellco Glass; Vineland, N.J.; vol.=250 ml) were inoculated with $2.0 \times 10^6$ PC3-MF cells/ml prostate carcinoma cells harvested by trypsinization (0.25% trypsin-EDTA; 37° C.; 10 minutes) from pre-confluent tissue culture flasks (Corning) in a final volume of 125 ml. Cells were gently disaggregated by continual pipetting prior to inoculation. Medium consisted of RPMI 1640 supplemented with 25 mM HEPES, 10% defined fetal bovine serum, plus 100 units/ml of penicillin and 100 μg/ml of streptomycin. Rotational speed was set to a minimal value of 60 rpm. On every fourth day, 40% of the conditioned medium was removed by pipette from the spinner flask and replaced with fresh medium. Media removed was routine centrifuged for 5 minutes at 600×g. Pelleted cells were resuspended in fresh media prewarmed to 37° C. and returned by pipette after gentle trituration to the spinner flask. Samples were collected at Day 10, 14, 20 and 24 of the experiment, washed twice with cold RPMI 1640 (without supplements), resuspended in cold RPMI 1640 16 h. in the presence of 1% (methanol-free) formaldehyde (4° C.; 16 hours).

C. Culturing of Prostate Cells Using Liquid-overlay Agarose Cultures

Liquid-overlay agarose cultures were initiated by utilizing a variation of the method first described by J. M. Yuhas, et al., "A simplified method for the production and growth of multicellular spheroids," *Cancer Res* 37:3639–3643 (1977). Six-well Falcon plates were coated with 2 ml of molten (55° C.) 1. Six-well Falcon plates were coated with 2 ml of molten (55° C.) 1.25% COMPATIGEL (FMC Bioproducts; Rockland, Me.), a low melting temp. agarose. The agarose had been suspended in 25 mM HEPES-buffered Hanks storage solution (pH 7.2) (GIBCO-BRL) and heated in a microwave oven for 45 seconds or until completely dissolved. The agarose was allowed to congeal overnight in a CEDCO (Portland, OR) incubator at 37° C., 100% humidity and in a 5% $CO_2$ atmosphere. The following day each well on the plate was inoculated by 10 ml pipette with $2 \times 10^5$ cells/ml PC3-MF prostate carcinoma cells harvested by trypsinization (0.25% trypsin-EDTA; 37° C.; 10 minutes) from pre-confluent tissue culture flasks (Corning) in a final volume of 5 ml. Every fourth day, 75% of the medium from each well was aspirated and replaced with fresh medium. Caution was taken not to remove any macroscopic aggregates that may have formed in the well. Samples were collected at Days 7, 14 and 21 of the experiment, washed twice with cold RPMI 1640 (without supplements), resuspended in cold RPMI 1640 16 h. in the presence of 1% (methanol-free) formaldehyde (4° C.; 16 hours).

D. Culturing of Two-Dimensional Monolayer Control Cultures

Two-dimensional monolayer controls were harvested for control biomarker expression with a cell scraper (Fisher Scientific; Pittsburgh, Pa.), washed two times in cold (4° C.) RPMI 1640 (without supplements). For surface antigen markers, cells were resuspended in cold RPMI 1640 overnight in the presence of 1% methanol-free formaldehyde (4° C.; 16 hours). For nuclear antigen markers for nuclear matrix protein (NMP-100) fluorescent immunocytochemistry, cells were fixed in 50% ethanol (instead of 0.5% formaldehyde) in RPMI 1640 (without supplements) and maintained for 16 hours at 4° C.

Biomarkers analyzed by these methods included the following: PD-41, p53, TCSF, c-erbB2, PSP-19, NMP100, TURP-27, and PSA. Results for some of the biomarkers are shown in Table 1 below. The numbers in Table 1 represent the percentage of cells positive for FITC fluorescence after correction for mouse isotype control on REPROMAN software. Each three-dimensional ("3D") culture is compared to a two-dimensional ("2D") culture, cultured and fixed concurrently. Each of the three-dimensional culture techniques demonstrated an increase in the percentage of cells positive for PD-41, p53, and TCSF biomarker expression over the corresponding two-dimensional culture technique.

A graphical comparison of biomarker expression rates in PC3-MF prostate adenocarcinoma cell line growth in a HARV bioreactor can be seen at FIG. 1. Percentages of the cells scoring positive for six different prostatic biomarkers by EPICS Elite Flow Cytometry are indicated on the y-axis. Cells were minced from PC3-MF spheroids fixed in 25% ethanol after being cultured in the HARV bioreactor for the number of days indicated on the x-axis.

TABLE 1

Percentage of Cells Positive for Biomarker Expression in 3-D and 2-D Cultures of Prostate Carcinoma Cells

| Type of 3-D culture | PD-41 2D | PD-41 3D | p53 2D | p53 3D | TCSF 2D | TCSF 3D | NMP100 2D | NMP100 3D | TURP-27 2D | TURP-27 3D | PSA 2D | PSA 3D |
|---|---|---|---|---|---|---|---|---|---|---|---|---|
| HARV (Day 14) | 1.29 | 1.92 | 13.8 | 33.0 | 1.0 | 0.32 | — | — | 1.2 | 0.58 | 0.76 | 0.36 |
| HARV (Day 21) | 1.50 | 27.9 | 2.48 | 74.0 | 2.48 | 32.2 | 86.0 | 98.0 | 2.5 | 0.36 | 4.0 | 1.32 |
| SPINNER Flask (Day 10) | 1.2 | 12.6 | 1.2 | 11.8 | 1.2 | 8.0 | — | — | — | — | 1.28 | 1.98 |
| SPINNER Flask (Day 14) | 0.3 | 8.5 | 0.9 | 28.2 | — | — | 86.0 | 97.5 | 2.56 | — | — | — |
| Liquid-overlay agarose (Day 10) | 0.3 | 0.8 | 0.9 | 13.0 | — | — | 86.0 | 97.6 | 12.4 | — | — | — |

Figure 2:
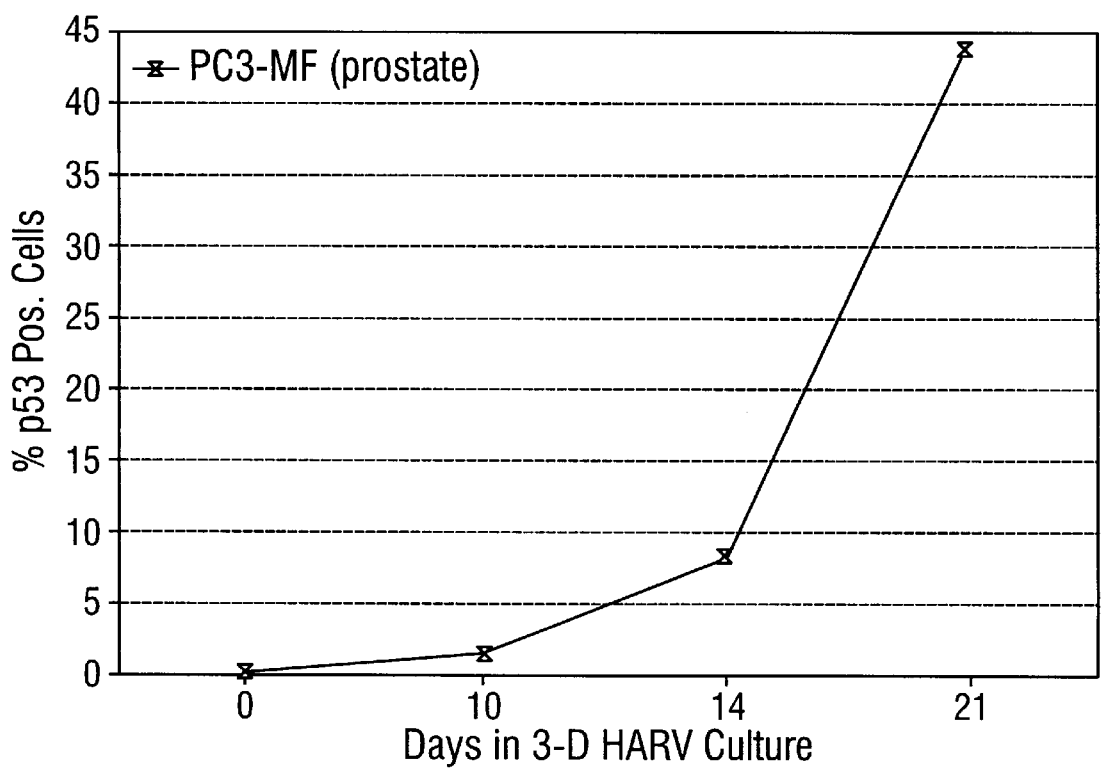
FIG. 2 is a graph depicting the percentage of cells positive for p53 antigen (clone 1801) expression in a three-dimensional culture of prostate carcinoma cell line PC3-MF in the HARV bioreactor measured over three weeks by flow cytometry.
Figure 3:
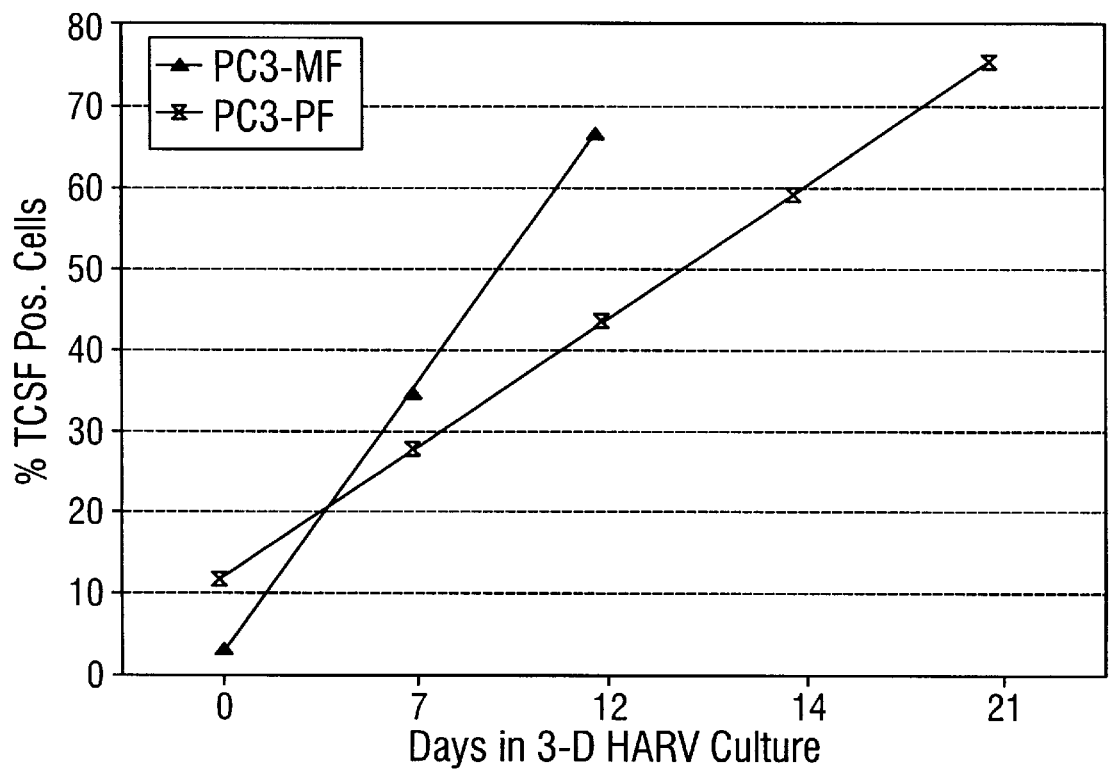
FIG. 3 is a graph depicting the percentage of cells positive for TCSF antigen expression in three-dimensional cultures of prostate carcinoma cell lines PC3-MF and PC3-PF in the HARV bioreactor measured over three weeks by flow cytometry.

Monolayers were kept in continuous two-dimensional culture for 21 days. The experiment was terminated on Day 21. The immunohistochemical procedures are indicated above. Overall, the biomarker expression rates were higher in the three-dimensional spheroidal cultures than in the two-dimensional monolayer cultures, and up-regulation of p53, PD-41, and c-erbB2 is exhibited. FIG. 2 further illustrates the up-regulation of p53 in the PC3-MF prostate adenocarcinoma cell line using the HARV three-dimensional culturing technique. FIG. 3 shows similar results for TCSF in both the PC3-MF and PC3-PF prostate adenocarcinoma cell lines.

EXAMPLE 2

Determination of Immunohistochemistry of Prostate Cell Cultures Using MATRIGEL™ Matrix Liquid-overlay Agarose Technique MATRIGEL™ matrix (Collaborative Biomedical Products, Becton Dickinson Labware, Two Oak Park, Bedford, Mass. 01730) was incorporated into three-dimensional liquid-overlay agarose technique and evaluated as to its effect on the differential expression of biomarkers in prostate cell cultures.

Liquid-overlay agarose cultures were initiated by adding molten (55° C.) 1.% COMPATIGEL (FMC Bioproducts; Rockland, Me.) to either six-well Falcon plates (2 ml/well) or 96-well microtiter plates (150 μl/well). The agarose had been suspended in 25 mM HEPES-buffered Hanks storage solution (pH 7.2) (GIBCO-BRL), heated in a microwave oven until completely dissolved, autoclaved for five minutes, poured into plates, and supplemented with penicillin, streptomycin and Fungizone upon cooling.

MATRIGEL™ matrix was utilized to prevent cells from settling to the bottom of a culture and attaching as a monolayer. Three methodologies were utilized in forming gel-cell aggregates with MATRIGEL™ matrix. In one method, 100 μl droplets of MATRIGEL™ matrix (4° C.) were formed through a truncated 500 μl pipette tip with an attached syringe and added to wells in a six-well liquid-overlay agarose culture plate described above. Immediately, $2 \times 10^5$ resuspended prostate carcinoma cells were added. In another method, $1 \times 10^6$ cells were resuspended in 1 ml MATRIGEL™ matrix (4° C.) and immediately dropped into wells in a six-well liquid-overlay agarose culture plate which was prewarmed to 37° C. In a third method, 200 μl MATRIGEL™ matrix (4° C.) was added to a spheroid containing cell preaggregates. The MATRIGEL™ matrix-containing spheroid was dropped through a wide-bore pipette or cannula into a well in a 96-well microtiter plate which was prewarmed to 37° C.

Upon inoculation, cells were allowed to aggregate over time with the addition of 10% fetal bovine serum and appropriate medium specific for the cell line three times per week.

Prior to assay, Dispase (Collaborative Biomedical Products) was used to disaggregate three-dimensional aggregates of cells which had been embedded in the MATRIGEL™ matrix. While Dispase is specific for MATRIGEL™ matrix dissolution, it can degrade extracellular matrix proteins upon prolonged exposure. The cell suspension was then centrifuged at 400×g for ten minutes. The cells were washed with Hanks storage solution, and viability was determined with 0.25% trypan blue.

The cultures were assayed for biomarker expression using flow cytometry as described in Example 1.

Figure 4:
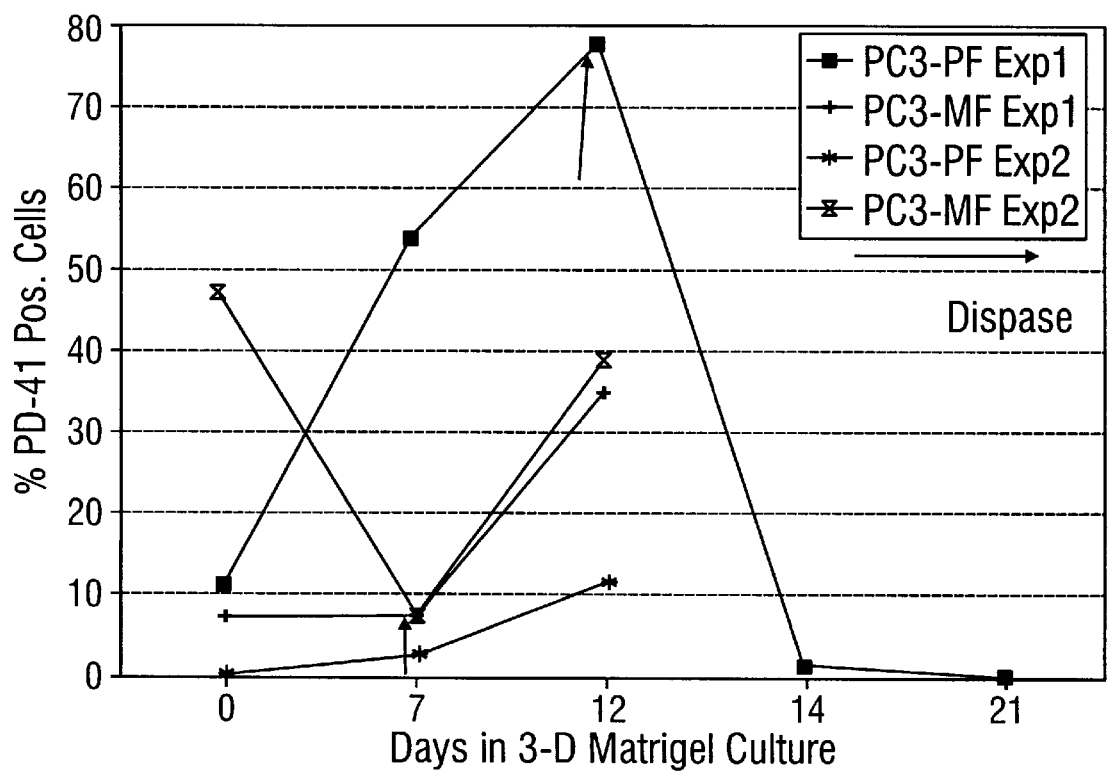
FIG. 4 is a graph depicting the percentage of cells positive for PD-41 expression in three-dimensional cultures of prostate carcinoma cell lines PC3-MF and PC3-PF embedded in MATRIGEL™ matrix on agarose-coated plates measured over three weeks by flow cytometry.
Figure 5:
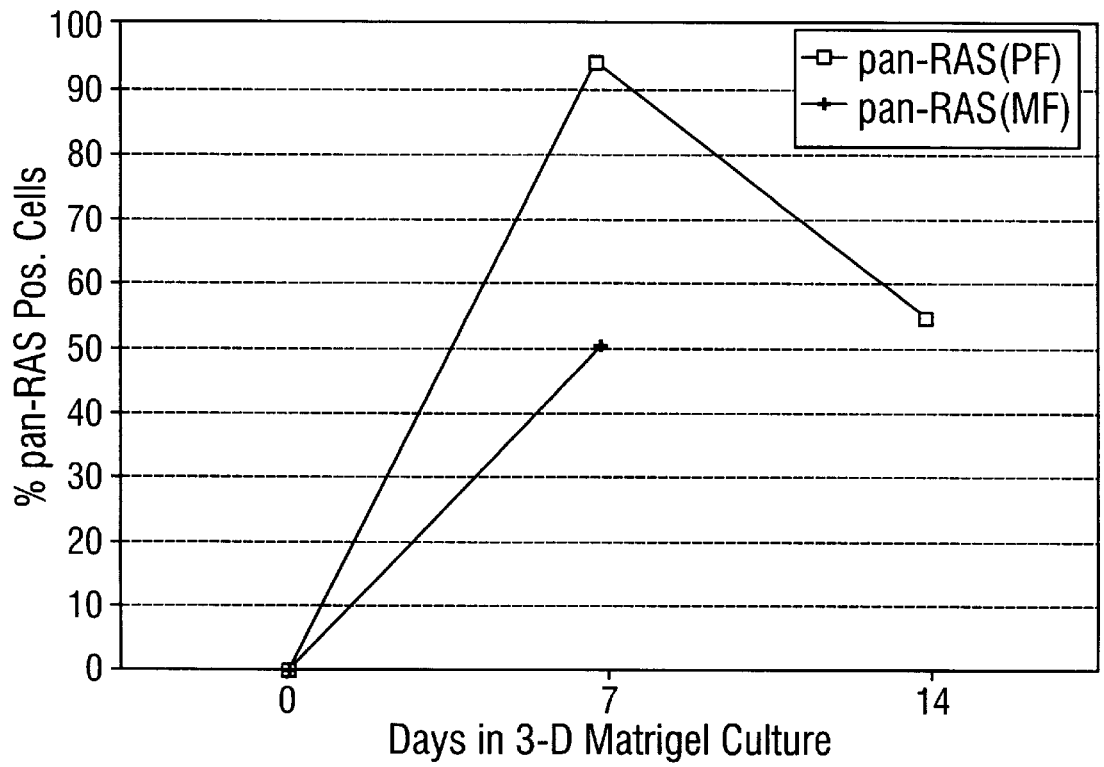
FIG. 5. is a graph depicting the percentage of cells positive for pan-ras antigen in three-dimensional cultures of prostate carcinoma cell lines PC3-MF and PC3-PF embedded in MATRIGEL™ matrix on agarose-coated plates measured over two weeks by flow cytometry.
Figure 6:
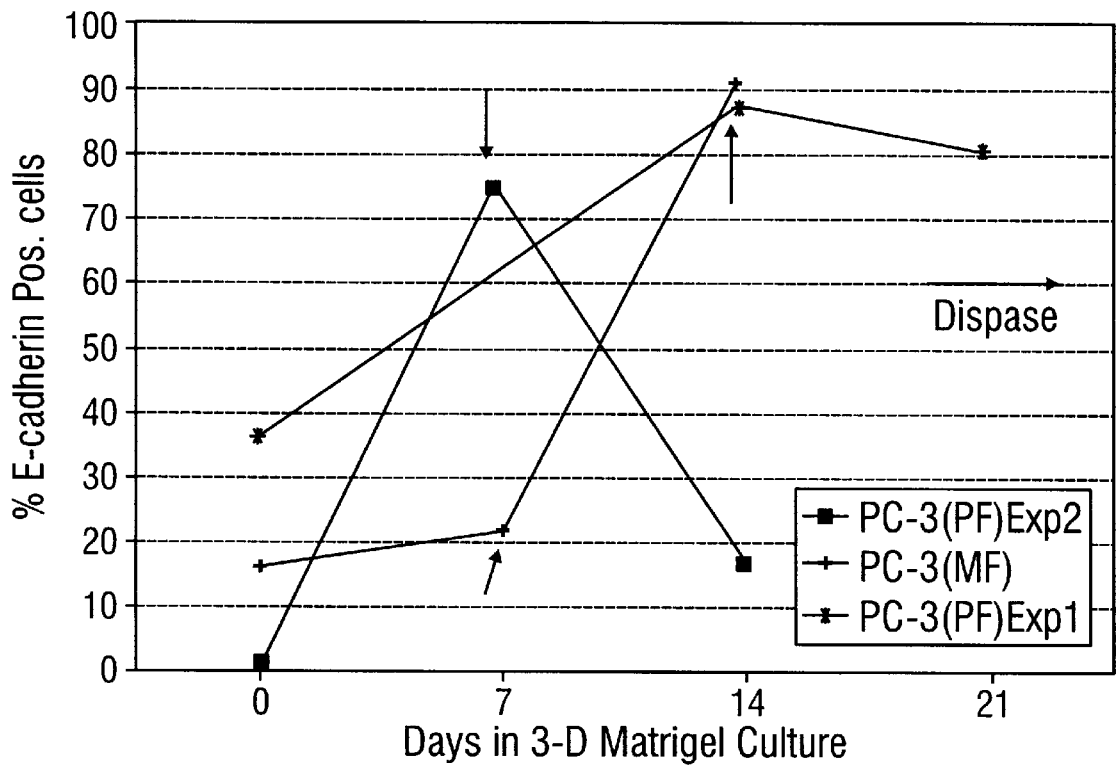
FIG. 6 is a graph depicting the percentage of cells positive for E-cadherin antigen expression in three-dimensional cultures of prostate carcinoma cell lines PC3-MF and PC3-PF embedded in MATRIGEL™ matrix on agarose-coated plates measured over three weeks by flow cytometry.

The MATRIGEL™ matrix liquid-overlay agarose three-dimensional culturing technique produced an overall increase in biomarker expression over time with the up-regulation of PD-41, pan-ras, and E-cadherin shown in FIG. 4–FIG. 6. FIG. 7 presents the down-regulation of AMFr.

For comparative purposes, monolayer cultures were prepared by overlaying monolayer colonies of prostate cancer cells in a 96-well microtiter plate with 9.3 micrograms/ml MATRIGEL™. The morphology of the three-dimensional cultures was spheroidal, and therefore more representative of actual tumor morphology. However, for the biomarkers tested and the conditions employed, significant differences in biomarker expression were not observed between the two culturing methods, indicating that MATRIGEL™ three-dimensional techniques appear to provide no advantages when compared to MATRIGEL™ monolayer cultures for selective induction of the tested biomarkers, although it is believed that overlaying the monolayer cultures with MATRIGEL™ may not be the appropriate control in this case. The MATRIGEL™ three-dimensional technique was found to be useful for biomarker expression over time and for tumor morphology.

EXAMPLE 3

Determination of Immunohistochemistry of Prostate Cell Cultures Using HARV Bioreactor Three-Dimensional Cultures Inoculated with Preaggregates from MATRIGEL™ Matrix Liquid-overlay Agarose Cultures Utilizing three dimensional MATRIGEL™ matrix liquid-overlay agarose technique, pre-aggregates malignant prostate carcinoma cell line PC3-MF cells were developed and then inoculated into the HARV bioreactor to evaluate the effect of pre-aggregate inoculation on the differential expression of biomarkers in prostate cell cultures.

Monolayers of malignant prostate carcinoma cell line PC3-MF cells were cultured and harvested as given in Example 1(A). Liquid-overlay agarose plates were prepared as given in Example 2, using 4 ml of 1.5% Compatigel agarose per well in 6-well plates. Harvested cells from the monolayer were mixed at $1 \times 10^6$ cells/ml with MATRIGEL™ matrix, and the liquid-overlay agarose plates were inoculated with the 1 ml of the MATRIGEL™/cell suspension. Cells were allowed to aggregate for seven days, feeding the liquid-overlay agarose cultures three times with RPMI 1640 medium supplemented with 10% fetal bovine serum.

After the seven day pre-aggregation period, the spheroids were removed from the growth medium and placed into 50 ml conical centrifuge tubes. The spheroid suspension was centrifuged at 1500 rpm for 10 minutes, and the supernatant removed. To the centrifuge tube, 5 ml of Dispase (Collaborative Biomedical Products) was added. The suspension was transferred to one well of a 6-well plate and incubated for two hours at 37° C. The Dispase was then neutralized with 10–15 ml of 10% fetal bovine serum RPMI 1640 medium. The cells were washed once with 0.5 mM ethylenediaminetetraacetic acid (EDTA) in PBS, centrifuged at 850–900 rpm for ten minutes, and the supernatant removed. The cells were washed with PBS followed by centrifugation at 850–900 rpm for ten minutes and removal of the supernatant; this washing procedure was repeated three more times. The washed cells were divided into two relatively equal volumes. One aliquot was counted and tested for viability using Trypan Blue exclusion dye. The other aliquot was added to the HARV bioreactor and processed as given in Example 1. The HARV bioreactor culture was sampled or harvested periodically. The spheroidal suspension was treated with Dispase, washed, and counted as described above for liquid-overlay agarose cultures, and following fixation, the cells were submitted for analysis by flow cytometry.

For comparative purposes, monolayers of PC3-MF cell; were prepared in 6-well plates containing MATRIGEL™ BIOCOAT™ (Collaborative Biomedical Products). After incubation, 2 ml of Dispase was added to each well and the plate was incubated for two hours at 37° C. The cell suspension was removed from the plate, placed into a 50 ml conical centrifuge tube, centrifuged at 1500 rpm for 10 minutes, and the supernatant aspirated. Dispase was neutralized by adding with 10–15 ml of 10% fetal bovine serum RPMI 1640 medium. The cells were washed once with 0.5 mM EDTA in PBS, centrifuged at 850–900 rpm for ten minutes, and the supernatant removed. The cells were washed with PBS followed by centrifugation at 850–900 rpm for ten minutes and removal of the supernatant; this washing procedure was repeated three more times. The washed cells were counted and tested for viability using Trypan Blue exclusion dye. Both three-dimensional and two-dimensional cultures were assayed for biomarker expression using flow cytometry as described in Example 1.

The percentage of biomarker expression was significant for cells which were pre-aggregated in the MATRIGEL™ liquid-overlay agarose culture prior to inoculation into the HARV bioreactor culture. FIG. 8 clearly depicts the up-regulation of c-erbB2 and the down-regulation of TURP-27 in the PC3-MF prostate adenocarcinoma cell line using the HARV bioreactor three-dimensional culturing technique.

EXAMPLE 4

Determination of Immunohistochemistry of Prostate Cell Cultures Following Chemotherapeutic Induction Using HARV Bioreactor Three-Dimensional Cultures Three-dimensional cell cultures can be utilized in a variety of ways as an evaluation tool. Cytotoxic chemotherapeutic agents for prostate cancer (e.g., adriamycin, methotrexate, 5-fluorouracil, suramin, cyclophosphamide) can be added to three-dimensional cell culture to evaluate individual or combination therapeutic regimens. The effects of chemotherapeutic induction by fenretinide and suramin on biomarker expression were determined.

Pre-aggregates of the prostate carcinoma cell lines PC3-MF and PC3-PF were prepared from liquid-overlay agarose cultures and harvested after seven days as given in Example 3. The pre-aggregates were then inoculated into a series of HARV bioreactors each of which contained RPMI-1640 growth medium supplemented with one of the following chemotherapeutic agents at one of the designated concentrations: fenretinide (4HPR) at 0, 0.05, 0.5, and 5 $\mu$M; and suramin at 0, 0.01, 0.1, and 1.0 mM. The cultures were subsequently sampled on Days 0, 5, and 10 according to the procedure specified in Example 3. The samples were assayed for biomarker expression using flow cytometry as described in Example 1.

Figure 10:
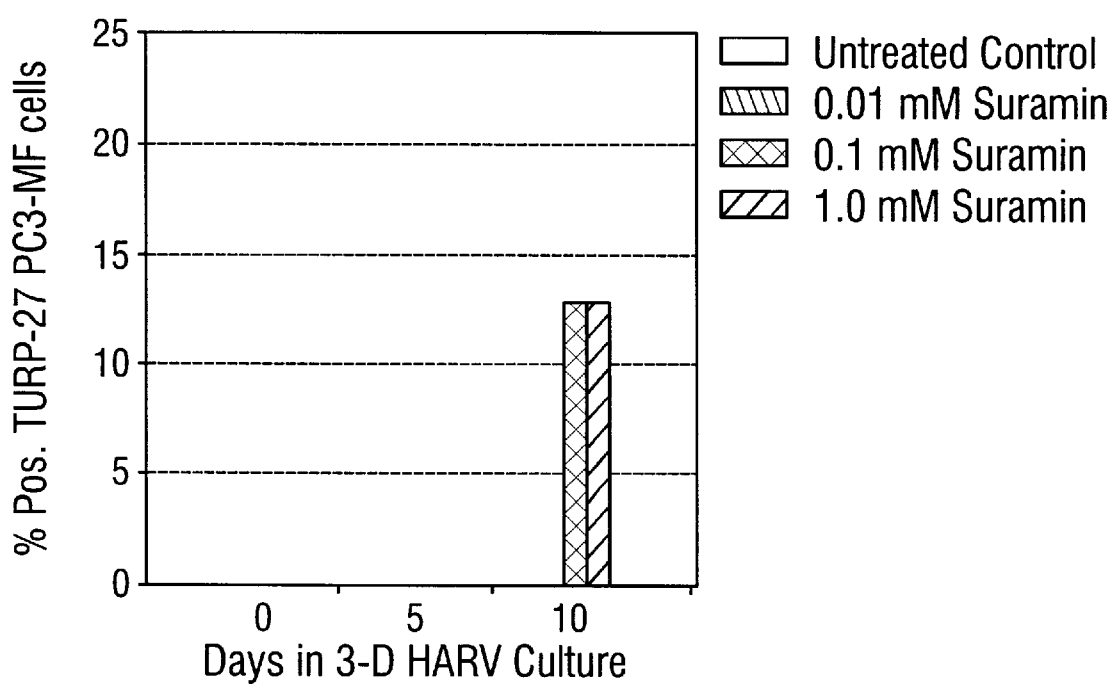
FIG. 10 is a graph depicting the induction of TURP-27 antigen expression by suramin in three-dimensional cultures of prostate carcinoma cell line PC3-MF in the HARV bioreactor measured over ten days by flow cytometry.
Figure 11:
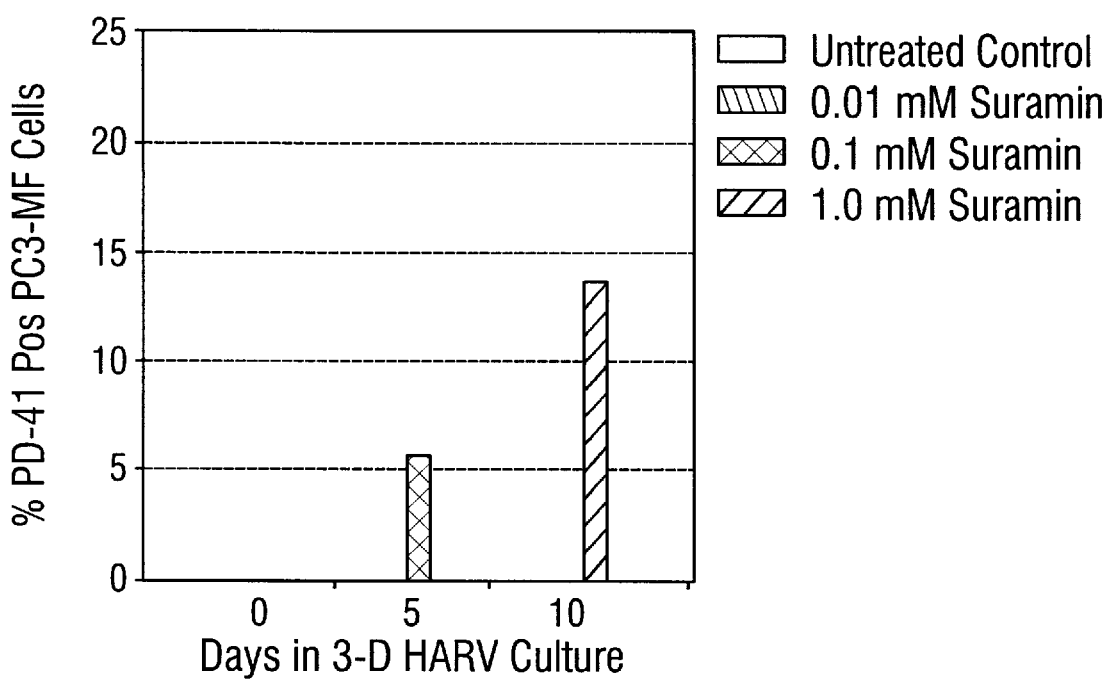
FIG. 11 is a graph depicting the induction of PD-41 antigen expression by suramin in three-dimensional cultures of prostate carcinoma cell line PC3-MF in the HARV bioreactor measured over ten days by flow cytometry.

FIG. 9 depicts the chemotherapeutic induction of TURP-27 biomarker expression in PC3-PF cells over time, indicating an absence of expression on Day 0 followed by expression in 100% of the PC3-PF cells by Day 5 with 0.5 and 5.0 $\mu$M fenretinide. TURP-27 expression was observed in PC3-MF cells by Day 10 with 0.1 and 1.0 mM suramin (FIG. 10). FIG. 11 shows the induction of PD-41 expression in PC3-MF cells by 0.1 mM suramin by Day 5.

EXAMPLE 5

Comparison of Three-dimensional and Two-dimensional Cultures for DNA and F-Actin Content The prostate monolayers and spheroidal aggregates from A–D of Example 1 were analyzed for DNA content and/or F-actin content using a Coulter EPICS II Profile Flow Cytometer or CAS-200 image system (Cell Image Systems, Elmhurst, Ill.). DNA content was determined by Feulgen stain and CAS-200 image analysis. (S. S. Bacus, et al., "HER-2/Neu oncogene expression and DNA ploidy analysis in breast cancer," *Arch Pathol Lab Med* 114:164–169 (1990). F-actin content was determined by flow cytometry using FITC conjugated phalloidin by the method of Rao, et al., "PL cellular F-actin levels as a marker for cellular transformation: relationship to cell division and differentiation," *Cancer Res* 50:2215–2220 (1990).

Both flow cytometric and CAS-200 image analyses (FIGS. 12 and 13) indicated that 21 day old spheroids expressed a significant aneuploid peak unlike the predominant diploid DNA content of their antecedent monolayer cultures.

Figure 12:
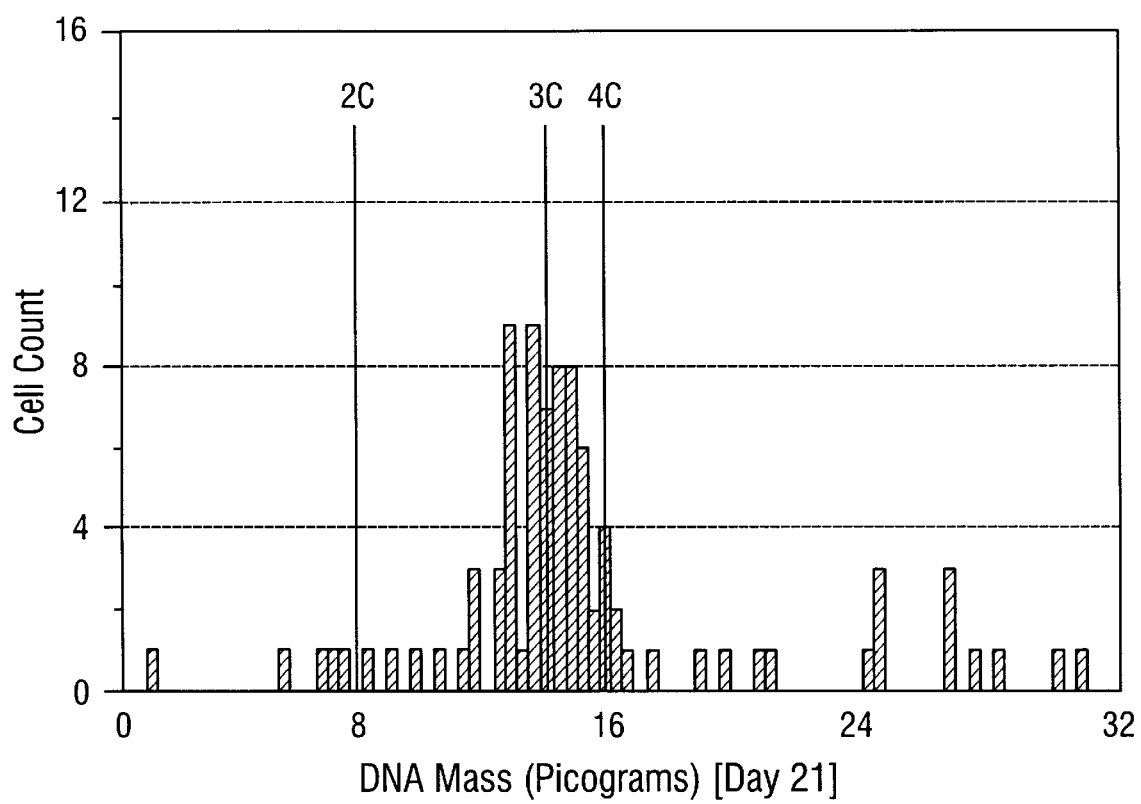
FIG. 12 is a histogram generated by the CAS-200 system which plots cell count against DNA mass for PC3-MF prostate adenocarcinoma cell line grown in monolayer (two-dimensional) culture.

FIG. 12 is a histogram generated by the CAS-200 system showing the DNA mass in picograms on Day 21 of PC3-MF prostate monolayer culture vs. cell count. A tetraploid DNA content was obtained. The aneuploid peak is represented by the "3C" peak.

Figure 13:
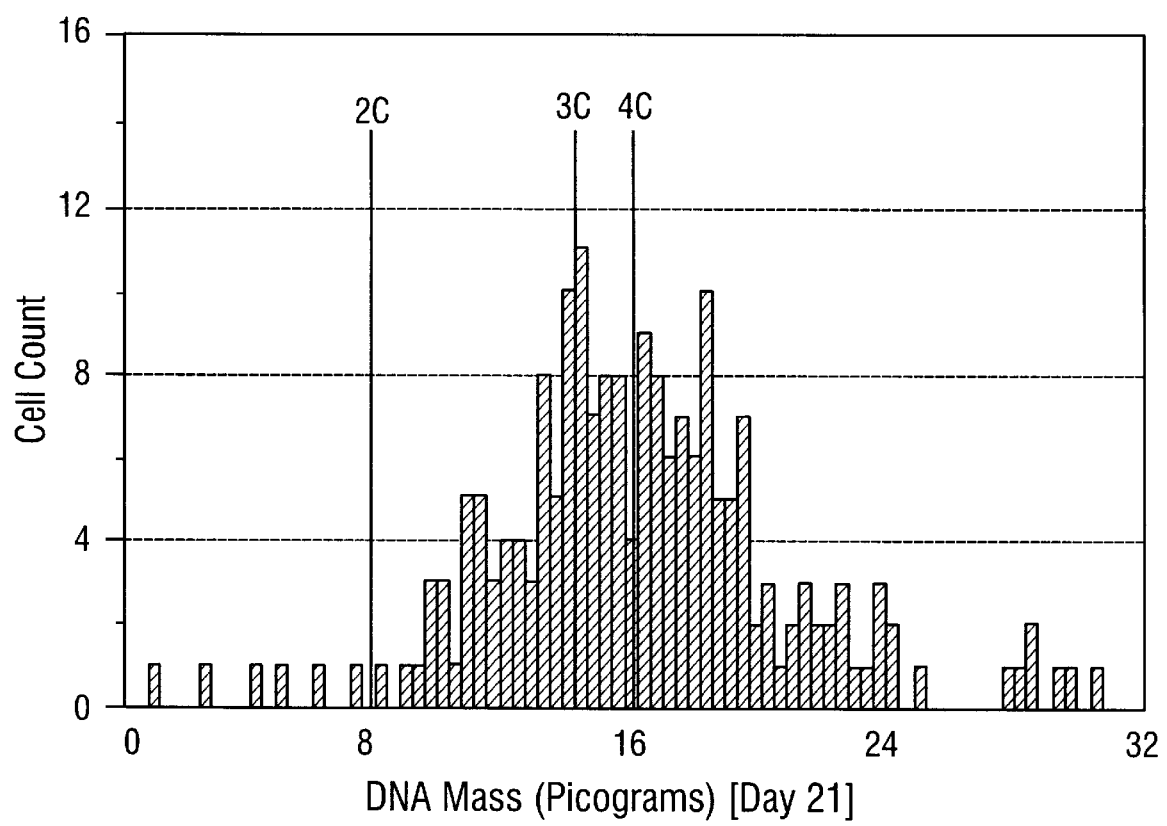
FIG. 13 is a histogram generated by the CAS-200 system which plots cell count against DNA mass for PC3-MF prostate adenocarcinoma cell line grown in spheroid culture (HARV bioreactor).

FIG. 13 is a CAS-200 system histogram demonstrating the DNA mass in picograms of PC3-MF prostate spheroid culture vs. cell count. A distinct aneuploid pattern for the sectioned spheroids is shown, with the aneuploid peak designated by the "3C" peak.

EXAMPLE 6

Comparison of Three-Dimensional Bladder Cell Cultures to Two-Dimensional Bladder Cell Cultures Differential expression of biomarkers was evaluated as a method of characterizing bladder cell cultures. Three-dimensional spheroidal aggregates of bladder cells (from culturing methodology given in A–C below) and two-dimensional monolayers (from culturing methodology given in D below) were harvested and processed simultaneously. Processing of bladder cells for flow cytometric analysis was performed according to the procedure given in Example 1.

A. Culturing of Bladder Cells Using The High Aspect Ratio Vessel (HARV):

Monolayers of bladder carcinoma cells (T-24) were cultured in large flat tissue culture flasks (Corning, Corning, N.Y.) were trypsinized (with 0.25% trypsin-EDTA), centrifuged at 1000 rpm in medium consisting of RPMI 1640 (Gibco-BRL) and supplemented with 25 mM HEPES, 10% defined fetal bovine serum (Hyclone, Logan, Utah), plus 100 units/ml of penicillin and 100 $\mu$g/ml of streptomycin. The High Aspect Rotating Vessel (HARV) was inoculated with 50 ml of the medium described above, pre-warmed to 37° C., into which had been resuspended $4.0 \times 10^5$ cells/ml. The vessel was rotated in a humidified 5% $CO_2$ incubator (37° C.) at a rate to maintain cellular aggregates in constant suspension. A pH of 7.2–7.3 was rigorously maintained during the three week culture period by daily replacement of 20 ml of conditioned culture medium with fresh medium. Vessel rotation rates were initially set at 40 rpm and adjusted to 22 rpm during the first 48 hours of the experiment in order to maintain suspension of growing spheroids and to minimize collisions with the vessel wall.

Procedures for harvesting bladder cells were the same as indicated in Example 1 for harvesting prostate cells.

B. Culturing of Bladder Cells Using Spinner Flask Cultures:

Spinner flask cultures were initiated by utilizing a variation of the method first applied by Moscona, *Exp Cell Res* 3:535 (1952). Spinner flasks (vol.=250 ml) were inoculated with $2.0 \times 10^6$ cells/ml T-24 bladder carcinoma cells harvested by trypsinization (0.25% trypsin-EDTA; 37° C.; 10 minutes) from pre-confluent tissue culture flasks (Corning) in a final volume of 125 ml. Medium consisted of McCoy's 5A supplemented with 25 mM HEPES, 10% defined fetal bovine serum plus 100 units/ml of penicillin and 100 $\mu$g/ml of streptomycin. Rotational speed was set to a minimal value of 60 rpm. On every fourth day, 40% of the conditioned medium was removed by pipette from the spinner flask and replaced with fresh medium. Media removed was routine centrifuged for 5 minutes at 600×g. Pelleted cells were resuspended in fresh media pre-warmed to 37° C. and returned by pipette after gentle trituration to the spinner flask. Samples were collected at Day 10, 14, 20 and 24 of the experiment, washed twice with cold RPMI 1640 (without supplements), resuspended in cold RPMI 1640 16 h. in the presence of 1% (methanol-free) formaldehyde (4° C.; 16 hours).

C. Culturing of Bladder Cells Using Liquid-overlay Agarose Cultures

Liquid-overlay agarose cultures were initiated by utilizing a variation of the method first described by Yuhas, et al., "A simplified method for the production and growth of multi-cellular spheroids," *Cancer Res* 37:3639–3643 (1977) Six-well Falcon plates were coated with 2 ml of molten (55° C.) 1.25% COMPATIGEL, a low melting temp. agarose. The agarose had been suspended in 25 mM HEPES-buffered Hank's storage solution (pH 7.2) and heated in a microwave oven for 45 seconds or until completely dissolved. The agarose was allowed to congeal overnight in a CEDCO (Portland, Oreg.) incubator at 37° C., 100% humidity and in a 5% $CO_2$ atmosphere. The following day each well on the plate was inoculated by 10 ml pipette with $2 \times 10^6$ cells/ml cells T-24 bladder carcinoma cells harvested by trypsinization (0.25% trypsin-EDTA; 37° C.; 10 minutes) from pre-confluent tissue culture flasks (Corning) in a final volume of 5 ml. Every fourth day, 75% of the medium from each well was aspirated and replaced with fresh medium. Caution was taken not to remove any macroscopic aggregates that may have formed in the well. Samples were collected at Day 7, 14, and 21 of the experiment, washed twice with cold RPMI 1640 (without supplements), resuspended in cold RPMI 1640 16 h. in the presence of 1% (methanol-free) formaldehyde (4° C.; 16 hours).]

D. Culturing of Two-Dimensional Monolayer Control Cultures

Two-dimensional monolayer controls were harvested for control biomarker expression with a cell scraper (Fisher Scientific; Pittsburgh, Pa.), washed two times in cold (4° C.) RPMI 1940 (without supplements). For surface antigen markers, cells were resuspended in cold RPMI 1640 overnight in the presence of 1% methanol-free formaldehyde (4° C.; 16 hours). For nuclear antigen markers fluorescent immunocytochemistry, cells were fixed in 50% ethanol (instead of 0.5% formaldehyde) in RPMI 1640 (without supplements) and maintained for 16 hours at 4° C.

Figure 14:
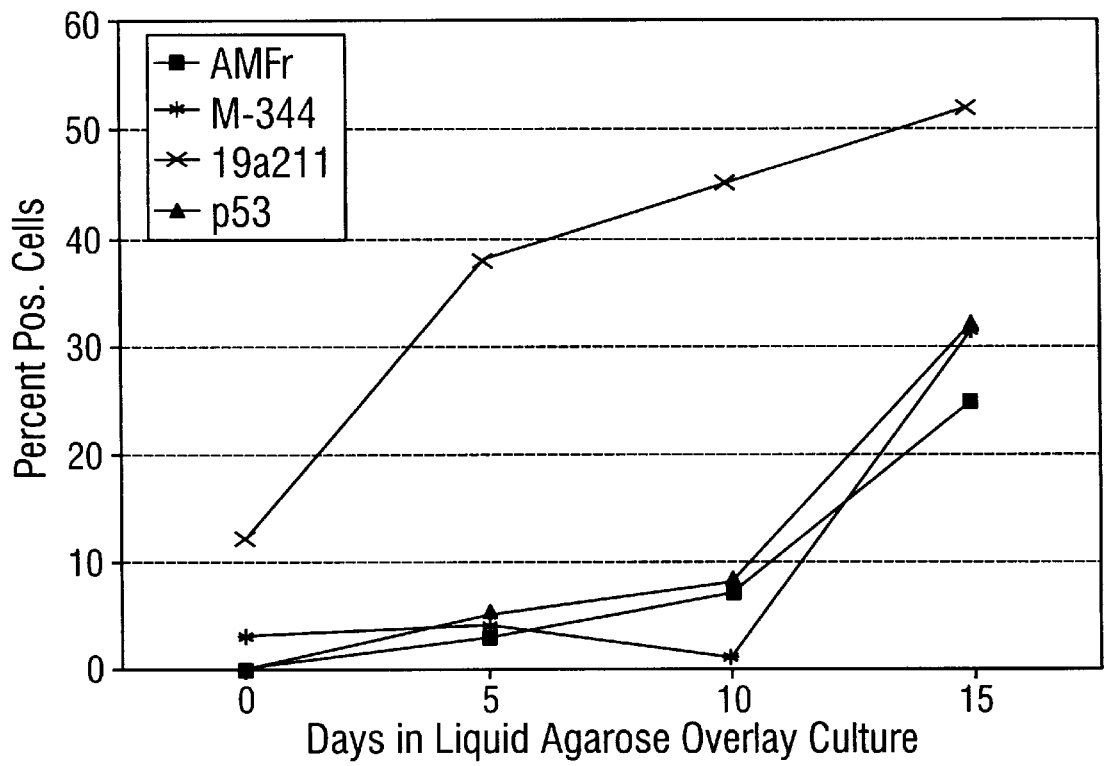
FIG. 14 is a graph depicting the percentage of cells positive for AMFr (automotility factor receptor), M-344, 19a211 and p53 antigen expression in three-dimensional cultures of bladder cancer cell line T24 in liquid agarose overlay culture measured over two weeks by flow cytometry.

The results for the three-dimensional liquid-overlay agarose cultures are given in FIG. 14. Up-regulation was observed for AMFr, M-344, 19a211, and p53 expression in T24 bladder cancer cells. The 19a211 biomarker was the most significantly modulated in the three-dimensional culture.

Figure 15:
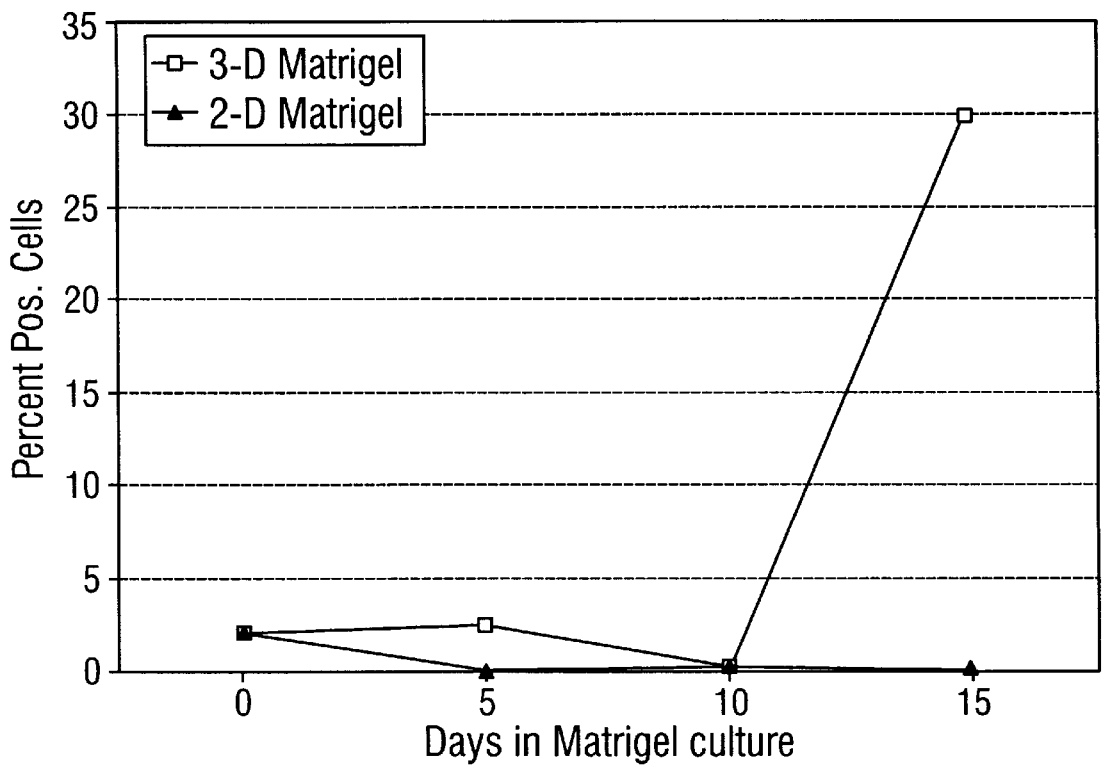
FIG. 15 is a graph depicting the percentage of cells, positive for M-344 expression in three-dimensional and two-dimensional MATRIGEL™ cultures of the bladder cancer cell line T24.

For the bladder cancer cells, there was a significantly higher expression of the M-344 bladder biomarker in the three-dimensional MATRIGEL™ cultures as opposed to the two-dimensional MATRIGEL™ cultures as depicted in FIG. 15. No significant differences were observed between the three-dimensional MATRIGEL™ cultures and the liquid agarose overlay technique as described by Yuhas, et al. (J. M. Yuhas, et al., "A simplified method for production and growth of multicellular tumor spheroids," *Cancer Res* 37:3639–3643 (1977))

EXAMPLE 7

Use of Three-dimensional Cultures to Test Hormonal Regulation of Cytotoxic Drugs Chemotherapeutic agents can be evaluated in vitro as single agents or a component of multi-drug regimens. Drugs to initiate apoptosis, or programmed cell death, and monoclonal antibody-drug conjugates can be assessed for efficacy. Cytotoxic T-lymphocytic clones can be tested. Cytokines can be evaluated for their biomodulatory effects, including biomarker induction. Hormonal or growth factor regulator drugs of cytotoxic drug-monoclonal antibody conjugates (e.g., androgen and 5-α-reductase inhibitors; anti-EGFr monoclonal-ricin conjugate) can be assessed in this model.

EXAMPLE 8

Use of Three-dimensional Cultures to Determine New Targets for Therapy

Three-dimensional growth can be used to unmask new targets for chemotherapies (e.g., oncogene products, mutant tumor suppressor gene products, signal transduction intermediates, cell adhesion molecules).

EXAMPLE 9

Use of Three-dimensional Cultures for Antigenic Modulation Leading to Therapy Identification Three-dimensional cell cultures can be used in antigenic modulation which can then be exploited for: (1) the development of autologous vaccines against antigens of interest (e.g., prostate mucin antigen); (2) the identification of tumor specific cytotoxic killer cells which can be expanded by cloning for potential therapeutic purposes; (3) identification and expansion of tumor-infiltration lymphocytes (TIL) and lymphocyte-activated Killer cells (LAK); (4) identification and expansion of T-cells producing specific cytokines; (5) identification and characterization of antigens shed during three-dimensional growth, leading to diagnostic assays for soluble factors in serum and or urine; and (6) identification and characterization of surrogate markers to act as chemoprevention or chemotherapeutic monitoring parameters and utilization of these surrogate markers in patient-specific protocols for chemoprevention, chemotherapeutics and monitoring.

In a preferred application, PD-41 (prostate mucin antigen) which is not produced in normal prostate tissue can be produced in three-dimensional culture of prostate tumor cells, isolated, and used to develop a vaccine which may protect against tumor cells. The three-dimensional culture may also be used to bind patient-produced antibodies or cytotoxic lymphocytes to the tumor biomarker, and these isolated patient substances can then be analyzed with techniques known in the art and the information derived used to produce substances for antibody/lymphocyte anticancer therapy.

We claim:

1. A method for inducing the production of prostate or bladder tumor-associated biomarkers comprising culturing prostate or bladder tumor cells using a low shear rotational three-dimensional tissue culture technique to form three-dimensional tissue cultures of said tumor cells under conditions effective for selectively inducing the expression of biomarkers or neoantigens associated with prostate or bladder cancers on the surface of said tumor cells and testing said three-dimensional cultures for said biomarkers or neoantigens.

2. The method of claim 1, wherein said tumor cells are neoplastic cell lines and wherein said low shear rotational three-dimensional tissue culture technique results in spheroidal aggregate cultures.

3. The method of claim 2, wherein said neoplastic cell lines are of prostate tissue origin.

4. The method of claim 2, wherein said neoplastic cell lines are of bladder tissue origin.

5. A method for assaying human tissue for the presence of prostate or bladder cancer markers, comprising the steps of:
   (a) obtaining a sample of human tissue subcultured as a primary cell line from a site containing neoplastic cells;
   (b) culturing said sample of human tissue using a low shear rotational three-dimensional cell culture technique to obtain a spheroidal aggregate culture; and
   (c) testing said spheroidal aggregate culture for at least one biomarker known to be associated with prostate or bladder cancer.

6. The method of claim 5, wherein said prostate cancer marker is selected from the group consisting of PD-41, p53, and TCSF.

7. The method of claim 5, wherein said bladder cancer marker is selected from the group consisting of AMFr, M-344, 19a21 1, and p53.

8. The method of claim 5, wherein said biomarker is F-actin content.

9. The method of claim 5, wherein said biomarker is DNA content.

10. A method for evaluating the efficacy of antineoplastic therapy on prostate or bladder tumor tissue, comprising:
   (a) obtaining a biopsy from a suspected tumor;
   (b) culturing said biopsy or a cell line derived therefrom using a low shear rotational three-dimensional tissue culture technique to form a spheroidal culture;
   (c) treating said spheroidal culture with an antineoplastic agent; and
   (d) determining the effect of said antineoplastic agent on the tumorigenicity of said spheroidal culture by monitoring quantitative changes in selected biomarker expression.

11. A method of isolating prostate or bladder tumor-specific cytotoxic lymphocytes or antibodies from a patient, comprising:
   (a) culturing a prostate or bladder tumor cell using a low shear rotational three-dimensional cell culture technique to form three-dimensional cell aggregates expressing a prostate or bladder tumor antigenic determinant;
   (b) incorporating said three-dimensional cell aggregates expressing said prostate or bladder tumor antigenic determinant into an assay;
   (c) exposing a biological sample from said patient to said three-dimensional cell aggregates expressing said prostate or bladder tumor antigenic determinant in said assay to form antigen-antibody or antigen-lymphocyte complexes with antibodies or lymphocytes present in said biological sample which are reactive with said prostate or bladder tumor antigenic determinant; and (d) isolating said antibodies or said lymphocytes from said antigen-antibody or said antigen-lymphocyte complexes in said assay.

12. The method according to claim 11, wherein a biological sample from a patient is obtained from said patient's peripheral blood, lymph nodes, carcinomal tissue or a combination thereof.

13. A method of producing a vaccine for immunization against a carcinoma, comprising:
   (a) culturing a prostate or bladder tumor cell using a low shear rotational three-dimensional cell culture technique to form three-dimensional cell aggregates expressing at least one prostate or bladder tumor antigenic determinant;
   (b) isolating at least one said prostate or bladder tumor antigenic determinant; and
   (c) developing a vaccine against at least one said prostate or bladder tumor antigenic determinant.

14. A method of producing a vaccine for autologous immunization of a patient against carcinoma, comprising:
   (a) culturing a prostate or bladder tumor cell from said patient using a low shear rotational three-dimensional cell culture technique to form three-dimensional cell aggregates expressing at least one prostate or bladder tumor antigenic determinant;
   (b) isolating at least one said prostate or bladder tumor antigenic determinant; and
   (c) developing a vaccine against at least one said prostate or bladder tumor antigenic determinant for immunizing said patient.

15. A method for inducing the production of prostate or bladder tumor-associated biomarkers comprising culturing prostate or bladder tumor cells using a low shear rotational three-dimensional tissue culture technique to form three-dimensional tissue cultures of said prostate or bladder tumor cells under conditions effective for selectively inducing the expression and secretion of biomarkers or neoantigens associated with prostate or bladder cancers and testing said three-dimensional cultures for said biomarkers or neoantigens.

16. The method of claim 15, wherein said tumor cells are neoplastic cell lines and wherein said low shear rotational three-dimensional tissue culture technique results in spheroidal aggregate cultures.

17. The method of claim 16, wherein the low shear rotational three-dimensional tissue culture technique is culturing in a bioreactor.

18. The method of claim 17 wherein the bioreactor is a high aspect ratio vessel.

19. The method of claim 2, wherein the low shear rotational three-dimensional tissue culture technique is culturing in a bioreactor.

20. The method of claim 19 wherein the bioreactor is a high aspect ratio vessel.

21. The method of claim 6 wherein the low shear rotational three-dimensional tissue culture technique is culturing in a bioreactor.

22. The method of claim 18 wherein the bioreactor is a high aspect rotating vessel.

23. A method for formulating a customized therapeutic strategy for treating a prostate or bladder cancer comprising the steps of:
   (a) obtaining a biopsy specimen from a prostate or bladder tumor;
   (b) culturing said biopsy specimen using a low shear rotational three-dimensional tissue culture technique to obtain a spheroidal culture;
   (c) determining the biomarker expression pattern of the spheroidal culture by testing said spheroidal culture for the presence or absence of one or more biomarkers known to be associated with said prostate or bladder cancer; and
   (d) comparing the biomarker expression pattern of the spheroidal culture of said biopsy specimen with that derived from an established cell line from said prostate or bladder cancer.

24. The method of claim 1, wherein said prostate tumor cells express PD-41, p53 or TCSF.

25. The method of claim 1, wherein said prostate cancer cells are obtained from a subject and expression of said markers is diagnostic of prostate cancer.

26. The method of claim 1, further comprising the steps of:
   determining the quantity of expression of said markers;
   contacting said cells with an antineoplastic agent; and
   determining the quantity of expression of said markers after said contact;
wherein a difference in the quantity of expression of said markers before and after contact with said antineoplastic agent is indicative of the efficacy of said antineoplastic agent in the treatment of said cancer cells.

27. The method of claim 1, further comprising contacting serum from a prostate cancer patient with said cells under conditions effective for immunoreactive binding of antibodies or cytotoxic lymphocytes from said serum to said cells and isolating said immunoreactive antibodies or cytotoxic lymphocytes.

* * * * *

UNITED STATES PATENT AND TRADEMARK OFFICE
CERTIFICATE OF CORRECTION

PATENT NO. : 5,856,112
DATED : January 5, 1999
INVENTOR(S) : Garry M. Marley and Robert W. Veltri It is certified that error appears in the above-identified patent and that said Letters Patent is hereby corrected as shown below:

Col. 18, line 31, please delete "19a21 1" and insert therefor -- 19a211 --.

Signed and Sealed this

Fourteenth Day of March, 2000

Attest:

Q. TODD DICKINSON

Attesting Officer    Commissioner of Patents and Trademarks